(12) United States Patent
Reiner et al.

(10) Patent No.: US 12,036,317 B2
(45) Date of Patent: Jul. 16, 2024

(54) READY TO USE DICLOFENAC STICK PACKS

(71) Applicant: APR APPLIED PHARMA RESEARCH SA, Balerna (CH)

(72) Inventors: Alberto Reiner, Como (IT); Giorgio Reiner, Como (IT)

(73) Assignee: APR APPLIED PHARMA RESEARCH SA, Balerna (CH)

( * ) Notice: Subject to any disclaimer, the term of this patent is extended or adjusted under 35 U.S.C. 154(b) by 241 days.

(21) Appl. No.: 17/584,212

(22) Filed: Jan. 25, 2022

(65) Prior Publication Data

US 2022/0218606 A1 Jul. 14, 2022

Related U.S. Application Data

(63) Continuation of application No. 16/713,052, filed on Dec. 13, 2019, now Pat. No. 11,260,026.

(60) Provisional application No. 62/779,514, filed on Dec. 14, 2018.

(51) Int. Cl.
| | |
|---|---|
| *A61K 9/08* | (2006.01) |
| *A61K 9/00* | (2006.01) |
| *A61K 31/196* | (2006.01) |
| *A61K 47/02* | (2006.01) |
| *A61K 47/26* | (2006.01) |

(52) U.S. Cl.
CPC .............. *A61K 9/08* (2013.01); *A61K 9/0053* (2013.01); *A61K 31/196* (2013.01); *A61K 47/02* (2013.01); *A61K 47/26* (2013.01)

(58) Field of Classification Search
None
See application file for complete search history.

*Primary Examiner* — Nannette Holloman
(74) *Attorney, Agent, or Firm* — Sterne, Kessler, Goldstein & Fox P.L.L.C.

(57) ABSTRACT

Ready to use liquid formulations of diclofenac potassium are disclosed which are particularly well suited for packaging in stick-packs.

25 Claims, 1 Drawing Sheet

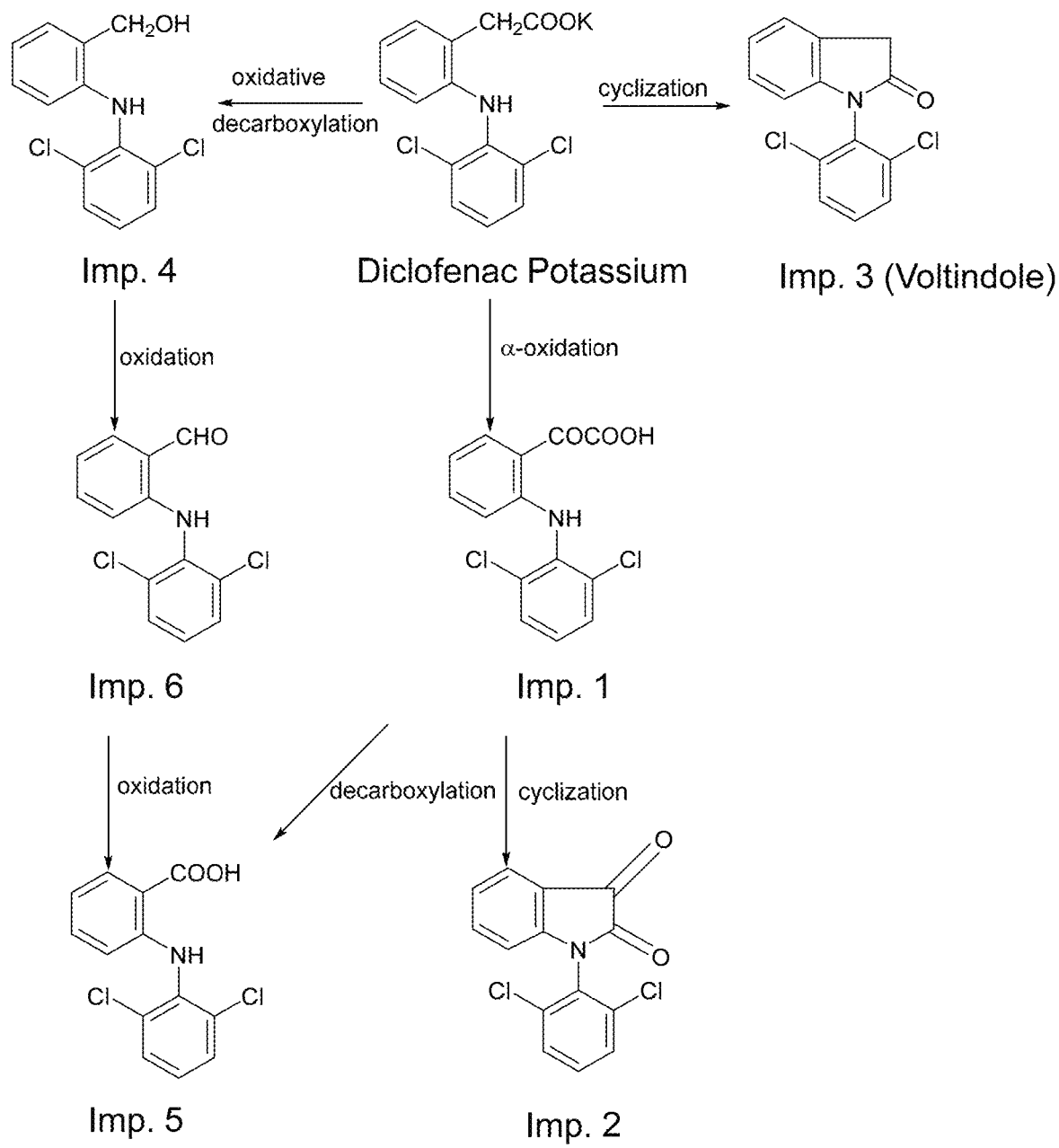

READY TO USE DICLOFENAC STICK PACKS

FIELD OF THE INVENTION

This invention pertains to a ready to use, liquid, orally administered formulations containing 50 mg of diclofenac potassium with unexpected chemical stability and palatability.

BACKGROUND OF THE INVENTION

Diclofenac potassium ([2-(2,6-dichlorophenyl)amino] benzeneacetate, potassium salt) is a potent NSAID (non-steroidal anti-inflammatory drug) used therapeutically for inflammatory conditions and pain management. The solubility of diclofenac potassium (pKa=3.9) is pH dependent. It is sparingly soluble at acidic pH, and the amount of the active substance dissolved in buffered solutions increases with the increasing pH of the dissolution aqueous medium. The stability of Diclofenac and its salts is well known in the solid state: Diclofenac acid and its salts are in fact characterized by a chemical stability when they are taken in their solid state. When dissolved in water, in contrast, the molecule could be expected to undergo fast and irreversible oxidative degradation according to the auto-oxidation pathway in FIG. 1.

Diclofenac is sold in various dosage forms, including tablets (Cataflam®), powders for oral solution (Cambia®), gel-caps (Zipsor®), patches (Flector®), and gels (Voltaren®). Other dosage forms are described, inter alia, in WO 2006/133954 (Reiner et al.), WO 1997/044023 (Reiner et al.), and WO 2003/043600 (Reiner et al.). Given its wide spectrum of action and therapeutic benefit, additional dosage forms are needed for convenience of the patient and additional therapeutic uses.

SUMMARY OF INVENTION

The inventors have developed a liquid, single dose, ready to use formulation containing diclofenac potassium as a unique active ingredient with the aim of obtaining a palatable and a chemically and physically stable water based oral solution. The stability of this unique liquid dosage form has been demonstrated in different primary packaging and under different storage conditions by preliminary stability studies, which showed that the impurities content conforms to rigorous pharmaceutical specifications even under accelerated conditions intended to induce degradation.

Therefore, one embodiment the invention provides a ready to use diclofenac formulation comprising: (a) diclofenac or a pharmaceutically acceptable salt thereof; (b) an alkalizing agent imparting a pH of from about 7 to about 10 to the formulation, optionally comprising potassium or sodium bicarbonate; and (c) a sugar-based aqueous means for solubilizing and stabilizing said formulation; wherein the formulation is optionally a liquid.

In another embodiment the invention provides a liquid diclofenac formulation in a ready to use stick pack comprising: (a) a therapeutically effective amount of diclofenac or a pharmaceutically acceptable salt thereof; (b) an alkalizing agent imparting a pH of from about 7 to about 10 to the formulation, optionally comprising potassium or sodium bicarbonate; and (c) a sugar-based aqueous means for solubilizing and stabilizing said formulation.

In still another embodiment the invention provides a method of treating a condition selected from pain and migraine in a patient in need thereof comprising administering to said patient a therapeutically effective amount of any of the ready to use diclofenac formulations of the present invention, preferably one comprising: (a) diclofenac or a pharmaceutically acceptable salt thereof; (b) an alkalizing agent imparting a pH of from about 7 to about 10 to the formulation, optionally comprising potassium or sodium bicarbonate; and (c) a sugar-based aqueous means for solubilizing and stabilizing said formulation, wherein the formulation is optionally provided as a liquid formulation in a ready to use stick pack.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawing, which is incorporated in and constitutes a part of this specification, illustrates several embodiments of the invention and together with the description serves to explain the principles of the invention.

FIG. 1 depicts various auto-oxidation pathways for diclofenac potassium.

DETAILED DESCRIPTION

Definitions and Use of Terms

As used in this specification and in the claims which follow, the singular forms "a," "an" and "the" include plural referents unless the context clearly dictates otherwise.

As used in this specification and in the claims which follow, the word "comprise" and variations of the word, such as "comprising" and "comprises," means "including but not limited to," and is not intended to exclude, for example, other additives, components, integers or steps. When an element is described as comprising a plurality components, steps or conditions, it will be understood that the element can also be described as comprising any combination of such plurality, or "consisting of" or "consisting essentially of" the plurality or combination of components, steps or conditions.

"Therapeutically effective amount" means that amount which, when administered to a human for supporting or affecting a metabolic process, or for treating or preventing a disease, is sufficient to cause such treatment or prevention of the disease, or supporting or affecting the metabolic process.

When ranges are given by specifying the lower end of a range separately from the upper end of the range, or specifying particular numerical values, it will be understood that a range can be defined by selectively combining any of the lower end variables, upper end variables, and particular numerical values that is mathematically possible. In like manner, when a range is defined as spanning from one endpoint to another, the range will be understood also to encompass a span between and excluding the two endpoints.

When used herein the term "about" will compensate for variability allowed for in the pharmaceutical industry and inherent in products in this industry, such as differences in product strength due to manufacturing variation and timeinduced product degradation. The term allows for any variation which in the practice of good manufacturing practices would allow the product being evaluated to be considered therapeutically equivalent or bioequivalent in humans to the recited strength of a claimed product.

In the context of the present invention insofar as it relates to any of the disease conditions recited herein, the term "treatment" means to reduce the occurrence of a symptom or condition, or to relieve or alleviate at least one symptom associated with such condition, or to slow or reverse the progression of such condition, or to manage or affect the metabolic processes underlying such condition. Within the meaning of the present invention, the terms also denote to arrest, delay the onset (i.e., the period prior to clinical manifestation of a disease) and/or reduce the risk of developing or worsening a disease.

The phrase "acceptable" as used in connection with compositions of the invention, refers to molecular entities and other ingredients of such compositions that are physiologically tolerable and do not typically produce untoward reactions when administered to a subject (e.g., a mammal such as a human).

DISCUSSION

In one embodiment the invention provides a ready to use diclofenac formulation comprising: (a) diclofenac or a pharmaceutically acceptable salt thereof; (b) an alkalizing agent imparting a pH of from about 7 to about 10 to the formulation, optionally comprising potassium or sodium bicarbonate; and (c) a sugar-based aqueous means for solubilizing and stabilizing said formulation; wherein the formulation is optionally a liquid.

In another embodiment the invention provides a liquid diclofenac formulation in a ready to use stick pack comprising: (a) a therapeutically effective amount of diclofenac or a pharmaceutically acceptable salt thereof; (b) an alkalizing agent imparting a pH of from about 7 to about 10 to the formulation, optionally comprising potassium or sodium bicarbonate; and (c) a sugar-based aqueous means for solubilizing and stabilizing said formulation.

In still another embodiment the invention provides a method of treating a condition selected from pain and migraine in a patient in need thereof comprising administering to said patient a therapeutically effective amount of any of the ready to use diclofenac formulations of the present invention, preferably one comprising: (a) diclofenac or a pharmaceutically acceptable salt thereof; (b) an alkalizing agent imparting a pH of from about 7 to about 10 to the formulation, optionally comprising potassium or sodium bicarbonate; and (c) a sugar-based aqueous means for solubilizing and stabilizing said formulation, wherein the formulation is optionally provided as a liquid formulation in a ready to use stick pack.

DISCUSSION OF EMBODIMENTS

In various embodiments the therapeutically effective amount comprises about 50 mg of diclofenac or a pharmaceutically acceptable salt thereof. In other embodiments therapeutically effective amount comprises about 50 mg of diclofenac or a pharmaceutically acceptable salt thereof in from about 8 to about 25 or 50 g of said formulation. In other embodiments the therapeutically effective amount comprises about 50 mg of diclofenac or a pharmaceutically acceptable salt thereof in from about 8 to about 15 g or from about 15 to about 50 g or from about 15 to about 22 g of said formulation. In still other embodiments the therapeutically effective amount comprises about 50 mg of diclofenac or a pharmaceutically acceptable salt thereof in about 20 g of said formulation. The preferred salt of diclofenac in all embodiments is diclofenac potassium.

The formulation, and particularly the sugar-based aqueous means, can be defined in various terms. Thus, in one embodiment the sugar-based aqueous means comprises a sugar selected from the group consisting of mono-, di-, tri-, and tetra-saccharides and sugar alcohols and combinations thereof. In another embodiment the sugar-based aqueous means is selected from the group consisting of monosaccharides, sugar alcohols, water and combinations thereof the monosaccharides are selected from the group consisting of glucose, fructose, and galactose; and the sugar alcohols are selected from the group consisting of ethylene and or propylene glycol; glycerol; erythritol; threitol; arabitol; xylitol; ribitol; mannitol; sorbitol; galactitol; fucitol; iditol; inositol; volemitol; isomalt; maltitol; lactitol; maltotriitol; maltotetraitol; and polyglycitol. In another embodiment the sugar-based aqueous means comprises a sugar selected from monosaccharides and sugar alcohols and combinations thereof the monosaccharides are selected from the group consisting fructose; and the sugar alcohols are selected from the group consisting of glycerol; erythritol; xylitol; sorbitol; and maltitol.

The formulations can be provided in stick packs as a liquid or a solid powder or granule that is subsequently reconstituted in water prior to administration. Thus, the sugar-based aqueous means can be a liquid, or it can refer to a solid which is compatible with water when subsequently reconstituted. When a liquid stick pack is intended, the "sugar-based aqueous means" will be preceded by "liquid."

The relative percentages of water and sugar in sugar-based aqueous means can vary, although it is generally preferable to have higher percentages of sugar. Thus, in some embodiments the sugar-based aqueous means comprises: from about 0% or 5% to about 95% water and from about 5% to about 95% of a sugar. In another embodiment the sugar-based aqueous means comprises from about 0% or 10% to about 60% water and from about 40% to about 90% of a sugar. In another embodiment the sugar-based aqueous means comprises from about 0% or 20% to about 40% water and from about 60% to about 80% of a sugar. In another embodiment the sugar-based aqueous means comprises: from 0% or 5% to about 95% water; and from about 5% to about 95% of a fruit sugar or monosaccharide or a combination thereof. In another embodiment the sugar-based aqueous means comprises: from about 0% or 10% to about 60% water; and from about 40% to about 90% of a fruit sugar or monosaccharide or a combination thereof. In another embodiment the sugar-based aqueous means comprises: from about 0% or 20% to about 40% water; and from about 60% to about 80% of a fruit sugar or monosaccharide or a combination thereof.

In another embodiment the sugar-based aqueous means comprises: from about 0% or 5% to about 95% water; and from about 5% to about 95% of a fruit sugar or monosaccharide or a combination thereof comprising: from about 10% to about 90% sorbitol; and from about 10% to about 90% of xylitol, maltitol, glycerol, fructose, erythritol or a combination thereof. In another embodiment the sugar-based aqueous means comprises: from about 0% or 10% to about 60% water; and from about 40% to about 90% of a fruit sugar or monosaccharide or a combination thereof comprising: from about 10% to about 90% sorbitol; and from about 10% to about 90% of xylitol, maltitol, glycerol, fructose, erythritol or a combination thereof. In another embodiment the sugar-based aqueous means comprises: from about 0% or 20% to about 40% water; and from about 60% to about 80% of a fruit sugar or monosaccharide or a combination thereof comprising: from about 10% to about 90% sorbitol; and from about 10% to about 90% of xylitol, maltitol, glycerol, fructose, erythritol or a combination thereof.

In another embodiment the sugar-based aqueous means comprises: from about 0% or 5% to about 95% water; and from about 5% to about 95% of sorbitol. In another embodiment the sugar-based aqueous means comprises: from about 0% or 10% to about 60% water; and from about 40% to about 90% of sorbitol. In another embodiment the sugar-based aqueous means comprises: from about 0% or 20% to about 40% water; and from about 60% to about 80% of sorbitol.

In another embodiment the sugar-based aqueous means comprises: from about 0% or 25% to about 75% water; and from about 25% to about 75% of xylitol. In another embodiment the sugar-based aqueous means comprises: from about 0% or 25% to about 75% water; and from about 25% to about 75% of maltitol. In another embodiment the sugar-based aqueous means comprises: from about 0% or 25% to about 75% water; and from about 25% to about 75% of glycerol. In another embodiment the sugar-based aqueous means comprises: from about 0% or 25% to about 75% water; and from about 25% to about 75% of fructose. In another embodiment the sugar-based aqueous means comprises: from about 0% or 55% to about 85% water; and from about 15% to about 45% of erythritol.

In some embodiments, a single sugar alcohol is included in the formulation selected from xylitol, maltitol, glycerin, erythritol, sorbitol, and non-crystallizing sorbitol. In other embodiments a combination of two sugar alcohols is included in the formulation selected from xylitol+sorbitol, xylitol+non-crystallizing sorbitol, maltitol+sorbitol, and maltitol+non-crystallizing sorbitol. When two sugar alcohols are present in combination, they are preferably present in a ratio of from about 10:90 to about 90:10.

In another embodiment the formulation comprises less than about 95% glycerol. In another embodiment the formulation is either substantially free of glycerol or completely free of glycerol. In another embodiment the formulation comprises less than about 15% ethanol. In another embodiment the formulation comprises less than about 2% ethanol. In still another embodiment the formulation is either substantially free of ethanol or completely free of ethanol.

Although bicarbonates ate preferred alkalizing agents, it will be understood that the formulations can contain any alkalizing agent, capable of producing the desired pH (preferably about 7.5 to about 10.0, or about 8.0 to about 9.0). Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

When a bicarbonate is used as the alkalizing agent, the formulations can also be defined more particularly in terms of the diclofenac and bicarbonate content of the formulation. Thus, in another embodiment the formulation comprises from about 0.1% to about 1% diclofenac or a pharmaceutically acceptable salt thereof; from about 0.05% to about 1.5% bicarbonate; and from 9 about 5% to about 99.85% of said sugar-based aqueous means. Once again, the diclofenac is preferably present as diclofenac potassium and the bicarbonate present as potassium bicarbonate.

In still another embodiment the formulation comprises from about 0.1% to about 1% diclofenac or a pharmaceutically acceptable salt thereof; from about 0.05% to about 1% bicarbonate or from about 0.1 to about 2% bicarbonate; and from about 95% to about 99.85% of said sugar-based aqueous means. Once again, the diclofenac is preferably present as diclofenac potassium and the bicarbonate present as potassium bicarbonate.

In another embodiment the formulation comprises additional ingredients selected from the group consisting of thickeners and sweeteners and taste modifying agents. In another embodiment the formulation comprises additional ingredients selected from the group consisting of sucralose, polyvinylpyrrolidone and hydroxyethylcellulose. Suitable taste-masking agents include cellulose hydroxypropyl ethers (HPC); low-substituted hydroxypropyl ethers (L-HPC); cellulose hydroxypropyl methyl ethers (HPMC); methylcellulose polymers; Ethylcelluloses (EC) and mixtures thereof; Polyvinyl alcohol (PVA); hydroxyethylcelluloses; carboxymethylcelluloses and salts of carboxymethylcelluloses (CMC); polyvinyl alcohol and polyethylene glycol co-polymers; monoglycerides, triglycerides, polyethylene glycols, modified food starch, acrylic polymers and mixtures of acrylic polymers with cellulose ethers; cellulose acetate phthalate; sepifilms such as mixtures of HPMC and stearic acid, cyclodextrins, and mixtures thereof.

Suitable flavoring agents include acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, *stevia*, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, and mixtures thereof.

In another embodiment the formulation of the present invention has a density of from about 1.02 to about 1.5 g/ml. In another embodiment the formulation of the present invention has a density of from about 1.05 to about 1.35 g/ml. In still another embodiment the formulation of the present invention has a density of from about 1.1 to about 1.25 g/ml.

The materials used to construct the laminate sheet for the stick pack can be any that are customary in the art, such as polyester, polypropylene, polyethylene and polyethylene terephthalate (PET), provided that the stick pack is sufficiently tear resistant until correctly manipulated. In preferred embodiments the laminate comprises a layer of aluminum foil. Examples of suitable designs for stick packs are described, for example in US 2015/0144518A1 and US20030168375A1. Suitable stick packs can also be purchased from companies such as Unette Corporation (Randolph New Jersey) and Amcor 360 Packaging Solutions (Melbourne Australia).

In another embodiment the formulation is present in a stick pack comprising a trilaminate of polyester, aluminum and polyethylene. In another embodiment the formulation is present in a stick pack comprising a trilaminate of polyester, aluminum and polyethylene, wherein said trilaminate: (a) has a layer thickness of 12/8.5/65 µm, respectively; (a) has a weight of 16.8/22.9/59.9 g/mq, respectively; (c) has micropores in the aluminum layer less than 300/mq.

In still other embodiments the formulation of the present invention has a pH of from about 7.5 to about 10.0. In another embodiment the formulation of the present invention has a pH of from about 8.0 to about 9.0.

In another embodiment the formulation of the present invention comprises less than about 1% total impurities. In another embodiment the formulation of the present invention has less than about 1% total impurities after storage at 40° C.±2° C. and 75% RH±5% RH for three or six months.

In another embodiment the diclofenac is present in the formulation as diclofenac potassium and the bicarbonate is present as potassium bicarbonate. In another embodiment the diclofenac is present in the formulation as diclofenac potassium and said bicarbonate is present as potassium bicarbonate at a weight ratio of from about 50:10 to about 50:100, about 50:10 to about 50:50, or about 50:50 to about 50:100, preferably about 50:22 or about 50:66.

In certain embodiments, the sugar-based aqueous means comprises sorbitol, and the sorbitol is either a crystallizing sorbitol solution or a non-crystallizing sorbitol solution, or a combination of both, as those terms are understood in the art and described in the United States Pharmacopoeia in effect on Dec. 1, 2019. In one particular embodiment the formulation comprises between 25% and 90% of a non-crystallizing sorbitol solution. In one particular embodiment the liquid formulation of the present invention comprise a sugar-based aqueous means contains both non-crystallizing sorbitol solution and crystallizing sorbitol solution.

In another embodiment the liquid formulation of the present invention comprises a sugar-based aqueous containing an antimicrobial agent.

In any of the embodiments and embodiments of the present invention, it will be understood that the formulation can be present as a liquid, and that the liquid will predominantly be water. Thus, in any of the embodiments and embodiments of this invention the formulation can be present as a liquid and the sugar based aqueous means comprise greater than about 5%, about 10%, or about 20% water. Alternatively, in any of the embodiments and embodiments of the invention the formulation can be present as a liquid, and the sugar based aqueous means comprise from about 5% to about 50% water or from about 10% to about 40% water. Alternatively, in any of the embodiments and embodiments of the invention the formulation can be present as a liquid comprising greater than about 5%, about 10%, or about 20% water. Alternatively, in any of the embodiments and embodiments of the invention the formulation is present as a liquid comprising from about 5% to about 50% water or from about 10% to about 40% water.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated and are intended to be purely exemplary of the invention and are not intended to limit the scope of what the inventors regard as their invention.

All the formulations/prototypes described herein have been tested for all or some of the following parameters: (1) Taste/Smell/Texture; (2) pH (3) Appearance; and (4) Assay and Impurities. Impurities were analyzed using two separate methods.

Assay and Impurity Method A (Impurities 1, 2, 3, 4, 6)
  ANALYTICAL EQUIPMENT: HPLC
  ANALYTICAL COLUMN: ALLTIMA C18 5 µm 250× 4.6 mm or equivalent
  MOBILE PHASE: 72.5% Methanol 27.5% buffer potassium dihydrogen
  phosphate (KH2PO4) 0.01M; Correct the mobile phase to pH 3.75±0.10 with phosphoric acid
  FLOW RATE: 1.3 mL/min
  WAVELENGTH: 256 nm
  INJECTED VOLUME: 20 µL
  TEMPERATURE: 30° C.
  ACQUISITION LENGTH: 25 minutes
  SOLVENT: Methanol
  Related Substance Retention Time:
  IMPURITY A (3): about 6.5 min
  IMPURITY B (6): about 15.0 min
  IMPURITY C (4): about 9.0 min
  IMPURITY 1: about 3.5 min
  IMPURITY 2: about 4.5 min
  DICLOFENAC K RETENTION TIME: about 11.0 minutes Impurity Profile (Impurity 5) Method B
  ANALYTICAL EQUIPMENT: HPLC
  ANALYTIC COLUMN: ALLTIMA C18 5 µm 250×4.6 mm or equivalent
  MOBILE PHASE: 60.0% Acetonitrile; 39.5% Water; 0.4% Phosphoric Acid; 0.1% Triethylamine; correct the mobile phase to pH 5.00±0.20 with Sodium Hydroxide 1N
  FLOW RATE: 1.2 mL/min
  WAVELENGTH: 256 nm
  INJECTED VOLUME: 20 µL TEMPERATURE COLUMN: 25° C.
  ACQUISITION LENGTH: 25 minutes
  IMPURITY 5: about 9.0 min
  DICLOFENAC K RETENTION TIME: about 8.0 minutes Total Impurities
  CALCULATE THE AMOUNT OF TOTAL IMPURITIES % by the formula: Impurities total %: Σ Impurities total % (Method A)+ΣImpurities total % (Method B);

Notes
  The reporting threshold for impurities is 0.1%, according to ICH Q3B_R2;
  The related substances retention times are indicative and referred to the main peak.

Stability Studies

All the formulations/prototypes manufactured and here below described have been stored under the following storage conditions:

| Storage conditions | |
| --- | --- |
| 25° C. ± 2° C./60% RH ± 5% | Long Term conditions |
| 30° C. ± 2° C./75% RH ± 5% RH | Intermediate conditions |
| 40° C. ± 2° C./75% RH ± 5% RH | Accelerated conditions |
| 5° C. | Back up conditions |

Primary Packaging

The following primary packaging has been evaluated for R&D stability purposes:
Amber Glass Vial 15 ml (filled with 8 ml of formula, leaving headspace of about 7 ml);
Stick packs used for stability testing were made of a Polyester/Aluminum/Polythene tri-layer laminate characterized by the following properties:
thickness 12/8.5/65µ
weight 16.8/22.9/59.9 g/mq
micropores for the Aluminum layer <300/mq Sorbitol The Non crystallizing Sorbitol Solution used in the following Examples is the Neosorb 70/70B® (Roquette) that complies with the USP-NF specifications related to non-crystallizing sorbitol solution. The characteristics of Neosorb 70/70B are as follows:
Anhydrous substance: 68.0-72.0%
Water: 28-32%
D-glucitol (D-sorbitol): 72.0-92.0% (Anhydrous substance)

The crystallizing sorbitol solution used in the following Examples is the Emprove® Essential (Merk) that complies with the USP-NF specifications related to crystallizing sorbitol solution. The characteristics of Emprove® Essential are as follows:
Anhydrous substance: 69.0-72.0%
Water: 28.5-31%
D-glucitol (D-sorbitol): 92.0-101.0% (Anhydrous substance)

Example 1 Liquid Oral Solution with Diclofenac and High Quantity of Sorbitol (Prototype PFS DK 27-bkT038/72)

The following formulation has been prepared to obtain a ready to use liquid solution containing 50 mg of Diclofenac in 20 g of formula.

Quali/Quantitative Formulation

| | Ingredient | mg/stick pack | % | g/bulk (1000 g) |
| --- | --- | --- | --- | --- |
| 1 | Diclofenac K | 50.0 | 0.25 | 2.5 |
| 2 | Potassium Bicarbonate (KHCO3) | 22.0 | 0.11 | 1.1 |
| 3 | Non crystallizing Sorbitol Solution | 19928.0 | 99.64 | 996.4 |
| | Total | 20000 | 100 | 1000.0 |

Manufacturing Method

Transfer the total quantity of Non crystallizing Sorbitol Solution in a glass container; treat the solution with nitrogen flow for about 30 minutes;
Add Potassium Bicarbonate and wait for the complete dissolution (about 5 minutes); maintain the system under stirring and under nitrogen flow;
Add Diclofenac Potassium and wait at least 2 hours maintaining the system under stirring and under nitrogen flow for all the time;
Filter the solution;
Store the solution in the selected container;
Treat the headspace of the container with nitrogen flow before close the container.

Analytical Evaluations

| | | | | |
| --- | --- | --- | --- | --- |
| | | Stability data | | |
| PFS DK27 - bkT038/72 | Tentative specifications | Time zero | Time 3 months 40° C., 75% RH Vials | Time 6 months 40° C., 75% RH Stick Pack |
| Appearance of the solution | Colourless clear solution | Complies | Slightly yellow clear solution | Pale yellow clear solution |
| pH (on sample, as it is) | To be defined | 8.44 | 8.45 | 8.22 |
| Diclofenac K Assay (%) | 95.0-105.0 | 98.8 | 97.5 | 97.1 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | 0.105 | — | — |
| Impurity B (6) (%) RRT = 1.39 | NMT 0.2 | — | — | — |
| Impurity 5 (%) RRT = 1.12 | NMT 0.2 | — | — | — |
| Total (known and unknown) impurities (%) | NMT 1.0 | 0.105 | — | — |

Example 2 Liquid Oral Solution with Diclofenac and Medium Quantity of Sorbitol (Prototype PFS DK 33-bkT038/87)

The following formulation has been prepared to obtain a ready to use liquid solution containing 50 mg of Diclofenac in 20 g of formula; a reduced concentration of sorbitol in comparison to Example 1 is tested.

Quali/Quantitative Formulation

|   | Ingredient | mg/stick pack | % | g/bulk (1000 g) |
|---|---|---|---|---|
| 1 | Diclofenac K | 50 | 0.250 | 2.5 |
| 2 | Potassium Bicarbonate (KHCO3) | 22 | 0.110 | 1.1 |
| 3 | Non crystallizing Sorbitol Solution | 14286 | 71.43 | 714.3 |
| 4 | Water | 5642 | 28.21 | 282.1 |
|   | Total | 20000 | 100.00 | 1000 |

Manufacturing Method

Transfer the total quantity of water and Non crystallizing Sorbitol Solution in a glass container; treat the solution with nitrogen flow for about 30 minutes;

Add Potassium Bicarbonate and wait for the complete dissolution (about 5 minutes); maintain the system under stirring and under nitrogen flow;

Add Diclofenac Potassium and wait at least 2 hours maintaining the system under stirring and under nitrogen flow for all the time;

Filter the solution;

Store the solution in the selected container;

Treat the headspace of the container with nitrogen flow before close the container.

Analytical Evaluations

| | | | Stability data | |
|---|---|---|---|---|
| PFS DK 33 - bkT038/87 | Tentative specifications | Time zero | Time 6 months 40° C., 75% RH Vials | Time 6 months 40° C., 75% RH Stick Pack |
| Appearance of the solution | Colourless clear solution | Complies | Yellow clear solution | Yellow clear solution |
| pH (on sample, as it is) | To be defined | 8.57 | 8.02 | 8.31 |
| Diclofenac K Assay (%) | 95.0-105.0 | 103.8 | 97.9 | 95.8 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | — | — | — |
| Impurity B (6) (%) RRT = 1.39 | NMT 0.2 | — | — | — |
| Impurity 5 (%) RRT = 1.12 | NMT 0.2 | — | 0.252 | 0.263 |
| UNK 15 (%) RRT = 0.550 | NMT 0.2 | — | 0.290 | — |
| Total (known and unknown) impurities (%) | NMT 1.0 | — | 0.542 | 0.263 |

Example 3 Liquid Oral Solution with Diclofenac and Low Quantity of Sorbitol (Prototype PFS DK 32-bkT038/86)

The following formulation has been prepared to obtain a ready to use liquid solution containing 50 mg of Diclofenac in 20 g of formula; a reduced concentration of sorbitol in comparison to Examples 1 and 2 has been tested.

Quali/Quantitative Formulation

|   | Ingredient | mg/stick pack | % | g/bulk (1000 g) |
|---|---|---|---|---|
| 1 | Diclofenac K | 50 | 0.25 | 2.5 |
| 2 | Potassium Bicarbonate (KHCO3) | 22 | 0.11 | 1.1 |
| 3 | Non crystallizing Sorbitol Solution | 7122 | 35.6 | 356.1 |
| 4 | Water | 12806 | 64.0 | 640.3 |
|   | Total | 20000 | 100.0 | 1000.0 |

Manufacturing Method

Transfer the total quantity of water and Non crystallizing Sorbitol Solution in a glass container; treat the solution with nitrogen flow for about 30 minutes;

Add Potassium Bicarbonate and wait for the complete dissolution (about 5 minutes); maintain the system under stirring and under nitrogen flow;

Add Diclofenac Potassium and wait at least 2 hours maintaining the system under stirring and under nitrogen flow for all the time;

Filter the solution;

Store the solution in the selected container;

Treat the headspace of the container with nitrogen flow before close the container.

Analytical Evaluations

Stability data

| PFS DK 32 - bkT038/86 | Tentative specifications | Time zero | Time 3 months 40° C., 75% RH Vials | Time 3 months 40° C., 75% RH Stick Pack |
|---|---|---|---|---|
| Appearance of the solution | Colourless clear solution | Complies | Pale yellow clear solution | Complies |
| pH (on sample, as it is) | To be defined | 8.63 | 8.56 | 8.31 |
| Diclofenac K Assay (%) | 95.0-105.0 | 102.9 | 97.6 | 97.7 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | — | 0.115 | 0.115 |
| Impurity B (6) (%) RRT = 1.39 | NMT 0.2 | — | — | — |
| Impurity 5 (%) RRT = 1.12 | NMT 0.2 | — | 0.133 | — |
| IMPURITY 15 (%) RRT = 0.550 | NMT 0.2 | — | 0.255 | — |
| Total (known and unknown) impurities (%) | NMT 1.0 | — | 0.503 | 0.115 |

Note:
The 6 months analyses were not performed due to the presence of mold in the samples

Example 4 Liquid Oral Solution with Diclofenac without Sorbitol (Prototype PFS DK 31-bkT038/85)

The following formulation has been prepared to obtain a ready to use liquid solution containing 50 mg of Diclofenac in 20 g of formula; the sorbitol syrup used for Examples 1, 2 and 3 is replaced with water.

Quali/Quantitative Formulation

| | Ingredient | mg/stick pack | % | g/bulk (1000 g) |
|---|---|---|---|---|
| 1 | Diclofenac K | 50.0 | 0.25 | 2.50 |
| 2 | Potassium Bicarbonate (KHCO3) | 22.0 | 0.11 | 1.10 |

-continued

| | Ingredient | mg/stick pack | % | g/bulk (1000 g) |
|---|---|---|---|---|
| 3 | Water | 19928.0 | 99.64 | 996.40 |
| | Total | 20000 | 100.0 | 1000.0 |

Manufacturing Method

Transfer the total quantity of water in a glass container; treat the solution with nitrogen flow for about 30 minutes;

Add Potassium Bicarbonate and wait for the complete dissolution (about 5 minutes); maintain the system under stirring and under nitrogen flow;

Add Diclofenac Potassium and wait at least 2 hours maintaining the system under stirring and under nitrogen flow for all the time;

Filter the solution;

Store the solution in the selected container;

Treat the headspace of the container with nitrogen flow before close the container.

Analytical Evaluations

Stability data

| PFS DK 31 - bkT038/85 | Tentative specifications | Time zero | Time 3 months 40° C., 75% RH Vials | Time 6 months 40° C., 75% RH Vials | Time 4 months 40° C., 75% RH Stick Pack | Time 6 months 40° C., 75% RH Stick Pack |
|---|---|---|---|---|---|---|
| Appearance of the solution | Colourless clear solution | Complies | Complies | Yellow clear solution | Complies | Yellow clear solution |
| pH (on sample, as it is) | To be defined | 9.00 | 9.24 | 9.30 | 8.94 | 9.10 |
| Diclofenac K Assay (%) | 95.0-105.0 | 103.8 | 97.7 | 97.1 | 97.7 | 96.0 |
| Impurity 1 (%) RRT = 0.38 | NMT 0.2 | — | 0.608 | 1.029 | — | — |
| Impurity 2 (%) RRT = 0.44 | NMT 0.2 | — | — | — | — | — |
| Impurity A (3) (%) RRT = 0.60 | NMT 0.2 | — | 0.293 | — | 0.183 | 0.333 |
| Impurity C (4) (%) RRT = 0.82 | NMT 0.2 | 0.101 | 0.249 | 0.242 | 0.282 | 0.238 |
| Impurity B (6) (%) RRT = 1.39 | NMT 0.2 | — | — | — | — | — |
| Impurity 5 (%) RRT = 1.12 | NMT 0.2 | — | — | 0.589 | — | 0.500 |
| Total (known and unknown) impurities (%) | NMT 1.0 | 0.101 | 1.150 | 1.860 | 0.465 | 1.071 |

Example 5 Liquid Oral Solution with Diclofenac and High Quantity of Sorbitol, without Nitrogen (Prototype PFS DK 34-bkT038/88)

The following formulation has been prepared to obtain a ready to use liquid solution containing 50 mg of Diclofenac in 20 g of formula. Differently from Example 1, the preparation has not been carried out under nitrogen.

15

Quail/Quantitative Formulation

|   | Ingredient | mg/stick pack | % | g/bulk (1000 g) |
|---|---|---|---|---|
| 1 | Diclofenac K | 50.0 | 0.25 | 2.50 |
| 2 | Potassium Bicarbonate (KHCO3) | 22.0 | 0.11 | 1.10 |
| 3 | Non crystallizing Sorbitol Solution | 19928.0 | 99.64 | 996.40 |
|   | Total | 20000 | 100 | 1000.0 |

Manufacturing Method

Transfer the total quantity of Non crystallizing Sorbitol Solution in a glass container;

Add Potassium Bicarbonate and wait for the complete dissolution (about 5 minutes); maintain the system under stirring;

Add Diclofenac Potassium and wait at least 2 hours maintaining the system under stirring;

Filter the solution;

Store the solution in the selected container.

Analytical Evaluations

16 in 20 g of formula. Differently from Example 2, the preparation is not carried out under nitrogen.

Quail/Quantitative Formulation

|   | Ingredient | mg/stick pack | % | g/bulk (1000 g) |
|---|---|---|---|---|
| 1 | Diclofenac K | 50 | 0.250 | 2.5 |
| 2 | Potassium Bicarbonate (KHCO3) | 22 | 0.110 | 1.1 |
| 3 | Non crystallizing Sorbitol Solution | 14286 | 71.43 | 714.3 |
| 4 | Water | 5642 | 28.21 | 282.1 |
|   | Total | 20000 | 100.00 | 1000 |

Manufacturing Method

Transfer the total quantity of water and Non crystallizing Sorbitol Solution in a glass container;

Add Potassium Bicarbonate and wait for the complete dissolution (about 5 minutes); maintain the system under stirring;

| | | | Stability data | |
|---|---|---|---|---|
| PFS DK 34 - bkT038/88 | Tentative specifications | Time zero | Time 3 months 40° C., 75% RH Vials | Time 6 months 40° C., 75% RH Stick Pack |
| Appearance of the solution | Colourless clear solution | Complies | Slightly yellow clear solution | Slightly yellow clear solution |
| pH (on sample, as it is) | To be defined | 8.19 | 8.38 | 8.01 |
| Diclofenac K Assay (%) | 95.0-105.0 | 101.9 | 97.8 | 95.6 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | — | — | — |
| Impurity B (6) (%) RRT = 1.39 | NMT 0.2 | — | — | — |
| Impurity 5 (%) RRT = 1.12 | NMT 0.2 | — | — | 0.154 |
| Total (known and unknown) impurities (%) | NMT 1.0 | — | — | 0.154 |

The Time 6 months analyses have been performed only on stick packs

Example 6 Liquid Oral Solution with Diclofenac and Medium Quantity of Sorbitol, without Nitrogen (Prototype PFS DK 42-bkT038/117)

The following formulation has been prepared to obtain a ready to use liquid solution containing 50 mg of Diclofenac Add Diclofenac Potassium and wait at least 2 hours maintaining the system under stirring;

Filter the solution;

Store the solution in the selected container.

Analytical Evaluations

| | | | Stability data | |
|---|---|---|---|---|
| PFS DK 42 - bkT038/117 | Tentative specifications | Time zero | Time 3 months 40° C., 75% RH Vials | Time 6 months 40° C., 75% RH Vials |
| Appearance of the solution | Colourless clear solution | Complies | Slightly yellow solution with mold floccules | Slightly yellow solution with reticulated mold |
| pH (on sample, as it is) | To be defined | n.d. | 8.59 | 8.57 |
| Diclofenac K Assay (%) | 95.0-105.0 | 99.1 | Not performed | Not performed |
| Impurity 1 (%) RRT = 0.38 | NMT 0.2 | — | | |
| Impurity 2 (%) RRT = 0.44 | NMT 0.2 | — | | |
| Impurity A (3) (%) RRT = 0.60 | NMT 0.2 | — | | |
| Impurity C (4) (%) RRT = 0.82 | NMT 0.2 | | | |

-continued

Stability data

| PFS DK 42 - bkT038/117 | Tentative specifications | Time zero | Time 3 months 40° C., 75% RH Vials | Time 6 months 40° C., 75% RH Vials |
|---|---|---|---|---|
| Impurity B (6) (%) RRT = 1.39 | NMT 0.2 | — | | |
| Impurity 5 (%) RRT = 1.12 | NMT 0.2 | — | | |
| Total (known and unknown) impurities (%) | NMT 1.0 | — | | |

Note: HPLC analyses have not been performed on samples that showed mold formation

Example 7 Liquid Oral Solution with Diclofenac and Low Quantity of Sorbitol, without Nitrogen (Prototype PFS DK 41-bkT038/116)

The following formulation has been prepared to obtain a ready to use liquid solution containing 50 mg of Diclofenac in 20 g of formula. Differently from Example 3, the preparation is not carried out under nitrogen.

Quali/Quantitative Formulation

| | Ingredient | mg/stick pack | % | g/bulk (1000 g) |
|---|---|---|---|---|
| 1 | Diclofenac K | 50 | 0.25 | 2.5 |
| 2 | Potassium Bicarbonate (KHCO3) | 22 | 0.11 | 1.1 |
| 3 | Non crystallizing Sorbitol Solution | 7122 | 35.6 | 356.1 |
| 4 | Water | 12806 | 64.0 | 640.3 |
| | Total | 20000 | 100.00 | 1000 |

Manufacturing Method

Transfer the total quantity of water and Non crystallizing Sorbitol Solution in a glass container;

Add Potassium Bicarbonate and wait for the complete dissolution (about 5 minutes); maintain the system under stirring;

Add Diclofenac Potassium and wait at least 2 hours maintaining the system under stirring;

Filter the solution;

Store the solution in the selected container.

Analytical Evaluations

Stability data

| PFS DK 41 - bkT038/116 | Tentative specifications | Time zero | Time 3 months 40° C., 75% RH Vials | Time 6 months 40° C., 75% RH Vials |
|---|---|---|---|---|
| Appearance of the solution | Colourless clear solution | Complies | Slightly yellow clear solution | Slightly yellow solution with reticulated mold |
| pH (on sample, as it is) | To be defined | n.d. | 8.75 | 8.73 |
| Diclofenac K Assay (%) | 95.0-105.0 | 100.5 | 99.7 | Not performed |
| Impurity 1 (%) RRT = 0.38 | NMT 0.2 | — | — | |
| Impurity 2 (%) RRT = 0.44 | NMT 0.2 | — | — | |
| Impurity A (3) (%) RRT = 0.60 | NMT 0.2 | — | — | |
| Impurity C (4) (%) RRT = 0.82 | NMT 0.2 | — | — | |
| Impurity B (6) (%) RRT = 1.39 | NMT 0.2 | — | — | |
| Impurity 5 (%) RRT = 1.12 | NMT 0.2 | — | — | |
| Total (known and unknown) impurities (%) | NMT 1.0 | — | — | |

Note:
HPLC analyses have not been performed on samples that showed mold formation

Example 8 Liquid Oral Solution with Diclofenac without Sorbitol (Prototype PFS DK 40-bkT038/115), without Nitrogen The following formulation has been prepared to obtain a ready to use liquid solution containing 50 mg of Diclofenac in 20 g of formula, using water as solvent. Differently from Example 4, the preparation is not carried out under nitrogen.

Quali/Quantitative Formulation

| | Ingredient | mg/stick | % | g/bulk (1000 g) |
|---|---|---|---|---|
| 1 | Diclofenac K | 50.0 | 0.25 | 2.50 |
| 2 | Potassium Bicarbonate (KHCO3) | 22.0 | 0.11 | 1.10 |
| 3 | Water | 19928.0 | 99.64 | 996.40 |
| | Total | 20000 | 100.0 | 1000.0 |

Manufacturing Method

Transfer the total quantity of water in a glass container;
Add Potassium Bicarbonate and wait for the complete dissolution (about 5 minutes); maintain the system under stirring;
Add Diclofenac Potassium and wait at least 2 hours maintaining the system under stirring;
Filter the solution;
Store the solution in the selected container.

Analytical Evaluations

Stability data

| PFS DK 40 - bkT038/115 | Tentative specifications | Time zero | Time 3 months 40° C., 75% RH Vials | Time 6 months 40° C., 75% RH Vials |
|---|---|---|---|---|
| Appearance of the solution | Colourless clear solution | Complies | Complies | Slightly yellow clear solution |
| pH (on sample, as it is) | To be defined | n.d. | 9.27 | 9.28 |
| Diclofenac K Assay (%) | 95.0-105.0 | 100.7 | 100.0 | 99.9 |
| Impurity 1 (%) RRT = 0.38 | NMT 0.2 | — | 0.445 | 1.608 |
| Impurity 2 (%) RRT = 0.44 | NMT 0.2 | — | — | — |
| Impurity A (3) (%) RRT = 0.60 | NMT 0.2 | — | 0.327 | 0.245 |
| Impurity C (4) (%) RRT = 0.82 | NMT 0.2 | 0.138 | 0.191 | 0.155 |
| Impurity B (6) (%) RRT = 1.39 | NMT 0.2 | — | — | — |
| Impurity 5 (%) RRT = 1.12 | NMT 0.2 | — | — | 0.376 |
| Total (known and unknown) impurities (%) | NMT 1.0 | 0.138 | 0.963 | 2.384 |

Example 9 Liquid Oral Solution with Diclofenac and Xylitol, with and without Nitrogen (Prototype PFS DK 46-bkT038/122 and Prototype PFS DK 43-bkT038/118)

The following formulations have been prepared to obtain a ready to use liquid solution containing 50 mg of Diclofenac in 20 g of formula; the sorbitol used in the previous examples is replaced with Xylitol in both the prototypes that have the same quali/quantitative formula but differ for the use of nitrogen during the manufacturing.

Quail/Quantitative Formulation

|  | Ingredient | mg/stick pack | % | g/bulk (2000 g) |
|---|---|---|---|---|
| 1 | Diclofenac K | 50 | 0.250 | 5.000 |
| 2 | Potassium Bicarbonate (KHCO3) | 22 | 0.110 | 2.200 |
| 3 | Xylitol | 10000 | 50.0 | 1000.0 |
| 4 | Water | 9928 | 49.6 | 992.8 |
|  | Total | 20000 | 100.00 | 2000 |

Manufacturing Method

PFS DK 46-bkT038/122

Transfer the total quantity of water and Xylitol in a glass container; treat the solution with nitrogen flow for about 30 minutes and wait for the complete dissolution;
Add Potassium Bicarbonate and wait for the complete dissolution (about 5 minutes); maintain the system under stirring and under nitrogen flow;
Add Diclofenac Potassium and wait at least 2 hours maintaining the system under stirring and under nitrogen flow for all the time;
Filter the solution;
Store the solution in the selected container;
Treat the headspace of the container with nitrogen flow before close the container.

PFS DK 43-BkT038/118

Transfer the total quantity of water and Xylitol in a glass container and wait for the complete dissolution;
Add Potassium Bicarbonate and wait for the complete dissolution (about 5 minutes); maintain the system under stirring;
Add Diclofenac Potassium and wait at least 2 hours maintaining the system under stirring;
Filter the solution;
Store the solution in the selected container.

Analytical Evaluations

| PFS DK 46 - bkT038/122 | Tentative specifications | Time zero | Time 3 months 25° C., 60% RH Vials | Time 6 months 40° C., 75% RH Stick Pack |
|---|---|---|---|---|
| Appearance of the solution | Colourless clear solution | Complies | Complies | Yellow clear solution |
| pH (on sample, as it is) | To be defined | 8.42 | 8.93 | 7.34 |
| Diclofenac K Assay (%) | 95.0-105.0 | 100.4 | 100.3 | 95.7 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | — | — | — |
| Impurity B (6) (%) RRT = 1.39 | NMT 0.2 | — | — | — |
| Impurity 5 (%) RRT = 1.12 | NMT 0.2 | — | — | — |
| Total (known and unknown) impurities (%) | NMT 1.0 | — | — | — |

| PFS DK 43 - bkT038/118 | Tentative specifications | Time zero | Time 3 months 25° C., 60% RH Vials | Time 6 months 40° C., 75% RH Stick Pack |
|---|---|---|---|---|
| Appearance of the solution | Colourless clear solution | Complies | Complies | Pale yellow clear solution |
| pH (on sample, as it is) | To be defined | 8.59 | 7.96 | 7.89 |
| Diclofenac K Assay (%) | 95.0-105.0 | 98.3 | 96.2 | 95.2 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | 0.133 |
| Impurity C (4) (%) RRT = 0.82 | NMT 0.2 | — | — | — |
| Impurity B (6) (%) RRT = 1.39 | NMT 0.2 | — | — | — |
| Impurity 5 (%) RRT = 1.12 | NMT 0.2 | — | — | — |
| Total (known and unknown) impurities (%) | NMT 1.0 | — | — | 0.133 |

Example 10 Liquid Oral Solution with Diclofenac, Maltitol and Sucralose, without Nitrogen (Prototype PFS DK 89-bkT038/174)

The following formulations have been prepared to obtain a ready to use liquid solution containing 50 mg of Diclofenac in 20 g of formula; maltitol and sucralose are here mixed with water to obtain the formula. The preparation is not carried out under nitrogen.

Quail/Quantitative Formulation

| | Ingredient | mg/stick pack | % | g/bulk (1000 g) |
|---|---|---|---|---|
| 1 | Diclofenac K | 50 | 0.250 | 2.5 |
| 2 | Potassium Bicarbonate (KHCO3) | 22 | 0.110 | 1.10 |
| 3 | Maltitol syrup 75% | 13333 | 66.7 | 666.65 |
| 4 | Water | 6583 | 32.9 | 329.15 |
| 5 | Sucralose | 12 | 0.0600 | 0.60 |
| | Total | 20000 | 100.00 | 1000 |

Manufacturing Method
  Transfer the total quantity of Maltitol syrup and water in a glass container;
  Add Sucralose and Potassium Bicarbonate and wait for the complete dissolution (about 5 minutes); maintain the system under stirring;
  Add Diclofenac Potassium and wait at least 2 hours maintaining the system under stirring;
  Filter the solution;
  Store the solution in the selected container.

Analytical Evaluations

| PFS DK 89 - bkT038/174 | Tentative specifications | Time zero | Time 3 months 40° C., 75% RH Vials | Time 6 months 40° C., 75% RH Vials |
|---|---|---|---|---|
| Appearance of the solution | Colourless clear solution | Complies | Slightly yellow clear solution | Slightly orange clear solution |

Stability data

| PFS DK 89 - bkT038/174 | Tentative specifications | Time zero | Time 3 months 40° C., 75% RH Vials | Time 6 months 40° C., 75% RH Vials |
|---|---|---|---|---|
| pH (on sample, as it is) | To be defined | 8.43 | 8.58 | 8.39 |
| Diclofenac K Assay (%) | 95.0-105.0 | 100.3 | 101.2 | 98.3 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | — | — | — |
| Impurity B (6) (%) RRT = 1.39 | NMT 0.2 | — | — | — |
| Impurity 5 (%) RRT = 1.12 | NMT 0.2 | — | — | 0.243 |
| Total (known and unknown) impurities (%) | NMT 1.0 | — | — | 0.243 |

Example 11 Liquid Oral Solution with Diclofenac and Glycerin, without Nitrogen (Prototype PFS DK 88-bkT038/173)

The following formulations have been prepared to obtain a ready to use liquid solution containing 50 mg of Diclofenac in 20 g of formula; glycerin is here used to obtain the formula. The preparation is not carried out under nitrogen.

Quail/Quantitative Formulation

| | Ingredient | mg/stick pack | % | g/bulk (1000 g) |
|---|---|---|---|---|
| 1 | Diclofenac K | 50 | 0.250 | 2.50 |
| 2 | Potassium Bicarbonate (KHCO3) | 22 | 0.110 | 1.10 |
| 3 | Glycerin | 10000.00 | 50.0 | 500.00 |
| 4 | Water added to 100% | 9916 | 49.6 | 495.80 |
| 5 | Sucralose | 12 | 0.0600 | 0.60 |
| | Total | 20000 | 100.00 | 1000.00 |

Manufacturing Method
 Transfer the total quantity of glycerin and water in a glass container;
 Add Sucralose and Potassium Bicarbonate and wait for the complete dissolution (about 5 minutes); maintain the system under stirring;
 Add Diclofenac Potassium and wait at least 2 hours maintaining the system under stirring;
 Filter the solution;
 Store the solution in the selected container.

Analytical Evaluations

Stability data

| PFS DK 88 - bkT038/173 | Tentative specifications | Time zero | Time 3 months 40° C., 75% RH Vials | Time 6 months 40° C., 75% RH Vials |
|---|---|---|---|---|
| Appearance of the solution | Colourless clear solution | Complies | Complies | Pale yellow clear solution |
| pH (on sample, as it is) | To be defined | 8.25 | 8.86 | 8.97 |
| Diclofenac K Assay (%) | 95.0-105.0 | 100.1 | 100.8 | 97.3 |
| Impurity 1 (%) RRT = 0.38 | NMT 0.2 | — | 0.109 | 0.176 |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | — | 0.126 | 0.117 |
| Impurity B (6) (%) RRT = 1.39 | NMT 0.2 | — | — | — |
| Impurity 5 (%) RRT = 1.12 | NMT 0.2 | — | — | — |
| Total (known and unknown) impurities (%) | NMT 1.0 | — | 0.235 | 0.293 |

Example 12 Liquid Oral Solution with Diclofenac and Erythritol without Nitrogen (Prototype PFS DK 90-bkT038/175)

The following formulations have been prepared to obtain a ready to use liquid solution containing 50 mg of Diclofenac in 20 g of formula; erythritol is here used to obtain the formula. The preparation is not carried out under nitrogen.

Quali/Quantitative Formulation

|   | Ingredient | mg/stick pack | % | g/bulk (500 g) |
|---|---|---|---|---|
| 1 | Diclofenac K | 50 | 0.25 | 1.25 |
| 2 | Potassium Bicarbonate (KHCO3) | 22 | 0.11 | 0.55 |
| 3 | Erythritol | 6000 | 30 | 150 |
| 4 | Water | 13916 | 69.58 | 347.9 |
| 5 | Sucralose | 12 | 0.06 | 0.3 |
|   | Total | 20000 | 100.00 | 500.00 |

Manufacturing Method
- Transfer the total quantity of water in a glass container;
- Add Erythritol, Sucralose and Potassium Bicarbonate and wait for the complete dissolution; maintain the system under stirring;
- Add Diclofenac Potassium and wait at least 2 hours maintaining the system under stirring;
- Filter the solution;
- Store the solution in the selected container.

Analytical Evaluations

| Stability data | | | | |
|---|---|---|---|---|
| PFS DK 90 - bkT038/175 | Tentative specifications | Time zero | Time 3 months 40° C., 75% RH Vials | Time 6 months 40° C., 75% RH Vials |
| Appearance of the solution | Colourless clear solution | Complies | Slightly yellow clear solution | Slightly yellow clear solution |
| pH (on sample, as it is) | To be defined | 8.68 | 7.31 | 7.02 |
| Diclofenac K Assay (%) | 95.0-105.0 | 100.5 | 99.3 | 95.4 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | — | — | — |
| Impurity B (6) (%) RRT = 1.39 | NMT 0.2 | — | — | — |
| Impurity 5 (%) RRT = 1.12 | NMT 0.2 | — | — | — |
| Total (known and unknown) impurities (%) | NMT 1.0 | — | — | — |

Example 13 Liquid Oral Solution with Diclofenac and Fructose, without Nitrogen (Prototype PFS DK 95-bkT038/186)

The following formulation has been prepared to obtain a ready to use liquid solution containing 50 mg of Diclofenac in 20 g of formula; water and fructose are here mixed to obtain the formula. The preparation is not carried out under nitrogen.

Quali/Quantitative Formulation

|   | Ingredient | mg/stick pack | % | g/bulk (500 g) |
|---|---|---|---|---|
| 1 | Diclofenac K | 50 | 0.25 | 1.25 |
| 2 | Potassium Bicarbonate (KHCO3) | 22 | 0.11 | 0.55 |
| 3 | Fructose | 10000 | 50.00 | 250.00 |
| 4 | Water | 9916 | 49.58 | 247.90 |
| 5 | Sucralose | 12 | 0.06 | 0.300 |
|   | Total | 20000 | 100.00 | 500.00 |

Manufacturing Method
- Transfer the total quantity of water in a glass container and dissolve the Fructose;
- Add Diclofenac K, sucralose and Potassium Bicarbonate and stir until complete dissolution;
- Filter the solution;
- Store the solution in the selected container.

Example 14 Liquid Oral Solution with Diclofenac and Non Crystallizing Sorbitol Solution—10 ml Volume (Prototype PFS DK 47-bkT038/123)

The following formulation has been prepared to obtain a ready to use liquid solution containing 50 mg of Diclofenac in, differently from Example 1, 12.5 g of formula. The preparation is not carried out under nitrogen.

Quali/Quantitative Formulation

|   | Ingredient | mg/stick pack | % | g/bulk (1000 g) |
|---|---|---|---|---|
| 1 | Diclofenac K | 50.0 | 0.40 | 4.0 |
| 2 | Potassium Bicarbonate (KHCO3) | 22.0 | 0.18 | 1.8 |
| 3 | Non crystallizing Sorbitol Solution | 12428.0 | 99.42 | 994.2 |
|   | Total | 12500 | 100.00 | 1000.0 |

Manufacturing Method
- Transfer the total quantity of Non crystallizing Sorbitol Solution in a glass container;

Add Potassium Bicarbonate and wait for the complete dissolution (about 5 minutes); maintain the system under stirring;
Add Diclofenac Potassium and wait at least 2 hours maintaining the system under stirring;
Filter the solution;
Store the solution in the selected container.

Analytical Evaluations

| PFS DK 47 - bkT038/123 | Tentative specifications | Time zero | Time 3 months 40° C., 75% RH Vials | Time 6 months 40° C., 75% RH Vials |
|---|---|---|---|---|
| Appearance of the solution | Colourless clear solution | Complies | Pale yellow clear solution | Orange clear solution |
| pH (on sample, as it is) | To be defined | — | 8.43 | 8.45 |
| Diclofenac K Assay (%) | 95.0-105.0 | 100.1 | 100.1 | 100.2 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | 0.150 |
| Impurity C (4) (%) RRT = 0.82 | NMT 0.2 | 0.138 | — | — |
| Impurity B (6) (%) RRT = 1.39 | NMT 0.2 | — | — | — |
| Impurity 5 (%) RRT = 1.12 | NMT 0.2 | — | — | — |
| Total (known and unknown) impurities (%) | NMT 1.0 | 0.138 | — | 0.150 |

Example 15 Liquid Oral Solution with Diclofenac, Sorbitol and Xylitol, with and without Nitrogen (Prototype PFS DK 49-bkT038/126 and Prototype PFS DK 44-bkT038/119)

The following formulations have been prepared to obtain a ready to use liquid solution containing 50 mg of Diclofenac in 20 g of formula; sorbitol and xylitol are here mixed for both the prototypes that have the same quali/quantitative formula but differ for the use of nitrogen during the manufacturing.

Quali/Quantitative Formulation

|   | Ingredient | mg/stick pack | % | g/bulk (2000 g) |
|---|---|---|---|---|
| 1 | Diclofenac K | 50 | 0.250 | 5.000 |
| 2 | Potassium Bicarbonate (KHCO3) | 22 | 0.110 | 2.200 |
| 3 | Non crystallizing Sorbitol Solution | 7142.8 | 35.7 | 714.3 |
| 4 | Xylitol | 5000 | 25.0 | 500.0 |
| 5 | Water added to 100% | 7785.2 | 38.9 | 778.5 |
|   | Total | 20000 | 100.00 | 2000 |

Manufacturing Method

PFS DK 49-BkT038/126
Transfer the total quantity of Non crystallizing Sorbitol Solution, Xylitol and water in a glass container; treat the solution with nitrogen flow for about 30 minutes;
Add Potassium Bicarbonate and wait for the complete dissolution (about 5 minutes); maintain the system under stirring and under nitrogen flow;
Add Diclofenac Potassium and wait at least 2 hours maintaining the system under stirring and under nitrogen flow for all the time;
Filter the solution;
Store the solution in the selected container;
Treat the headspace of the container with nitrogen flow before close the container.

PFS DK 44-bkT038/119
Transfer the total quantity of Non crystallizing Sorbitol Solution, Xylitol and water in a glass container;
Add Potassium Bicarbonate and wait for the complete dissolution (about 5 minutes); maintain the system under stirring;
Add Diclofenac Potassium and wait at least 2 hours maintaining the system under stirring;
Filter the solution;
Store the solution in the selected container.

Analytical Evaluations

| PFS DK 49 - bkT038/126 | Tentative specifications | Time zero | Time 3 months 25° C., 60% RH Vials | Time 3 months 40° C., 75% RH Vials |
|---|---|---|---|---|
| Appearance of the solution | Colourless clear solution | Complies | Complies | Slightly yellow clear solution |
| pH (on sample, as it is) | To be defined | 8.48 | 8.77 | 8.75 |
| Diclofenac K Assay (%) | 95.0-105.0 | 100.2 | 98.6 | 97.6 |
| Impurity 1 (%) RRT = 0.38 | NMT 0.2 | — | — | — |
| Impurity 2 (%) RRT = 0.44 | NMT 0.2 | — | — | — |

-continued

Stability Data

| PFS DK 49 - bkT038/126 | Tentative specifications | Time zero | Time 3 months 25° C., 60% RH Vials | Time 3 months 40° C., 75% RH Vials |
|---|---|---|---|---|
| Impurity A (3) (%) RRT = 0.60 | NMT 0.2 | — | — | — |
| Impurity C (4) (%) RRT = 0.82 | NMT 0.2 | 0.100 | 0.189 | 0.189 |
| Impurity B (6) (%) RRT = 1.39 | NMT 0.2 | — | — | — |
| Impurity 5 (%) RRT = 1.12 | NMT 0.2 | — | — | 0.145 |
| UNK 4 (%) RRT = 0.578 | NMT 0.2 | — | — | 0.136 |
| Total (known and unknown) impurities (%) | NMT 1.0 | 0.100 | 0.189 | 0.470 |

Example 16 Liquid Oral Solution with Diclofenac, Sorbitol and Xylitol, with and without Nitrogen (Prototype PFS DK 48-bkT038/125 and Prototype PFS DK 45-bkT038/121)

The following formulations have been prepared to obtain a ready to use liquid solution containing 50 mg of Diclofenac in 20 g of formula; sorbitol and xylitol are here mixed for both the prototypes that have the same quali/quantitative formula but differ for the use of nitrogen during the manufacturing.

|   | Ingredient | mg/stick pack | % | g/bulk (2000 g) |
|---|---|---|---|---|
| 1 | Diclofenac K | 50 | 0.250 | 5.000 |
| 2 | Potassium Bicarbonate (KHCO3) | 22 | 0.110 | 2.200 |
| 3 | Non crystallizing Sorbitol Solution | 14285.7 | 71.4 | 1428.6 |
| 4 | Xylitol | 4000 | 20.0 | 400.0 |
| 5 | Water added to 100% | 1642.3 | 8.2 | 164.2 |
|   | Total | 20000 | 100.0 | 2000 |

Manufacturing Method

PFS DK 48-bkT038/125

Transfer the total quantity of Non crystallizing Sorbitol Solution, Xylitol and water in a glass container; treat the solution with nitrogen flow for about 30 minutes;

Add Potassium Bicarbonate and wait for the complete dissolution (about 5 minutes); maintain the system under stirring and under nitrogen flow;

Add Diclofenac Potassium and wait at least 2 hours maintaining the system under stirring and under nitrogen flow for all the time;

Filter the solution;

Store the solution in the selected container;

Treat the headspace of the container with nitrogen flow before close the container.

PFS DK 45-bkT038/121

Transfer the total quantity of Non crystallizing Sorbitol Solution, Xylitol and water in a glass container;

Add Potassium Bicarbonate and wait for the complete dissolution (about 5 minutes); maintain the system under stirring;

Add Diclofenac Potassium and wait at least 2 hours maintaining the system under stirring;

Filter the solution;

Store the solution in the selected container.

Analytical Evaluations

Stability data

| PFS DK 48 - bkT038/125 | Tentative specifications | Time zero | Time 3 months 25° C., 60% RH Vials | Time 3 months 40° C., 75% RH Vials |
|---|---|---|---|---|
| Appearance of the solution | Colourless clear solution | Complies | Complies | Slightly yellow clear solution |
| pH (on sample, as it is) | To be defined | 8.57 | 8.76 | 8.77 |
| Diclofenac K Assay (%) | 95.0-105.0 | 101.4 | 100.2 | 102.1 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | — | — | 0.104 |
| Impurity B (6) (%) RRT = 1.39 | NMT 0.2 | — | — | — |
| Impurity 5 (%) RRT = 1.12 | NMT 0.2 | — | — | — |
| Total (known and unknown) impurities (%) | NMT 1.0 | — | — | 0.104 |

Stability data

| PFS DK 45 - bkT038/121 | Tentative specifications | Time zero | Time 3 months 25° C., 60% RH Vials | Time 3 months 40° C., 75% RH Vials |
|---|---|---|---|---|
| Appearance of the solution | Colourless clear solution | Complies | Complies | Slightly yellow clear solution |
| pH (on sample, as it is) | To be defined | 8.49 | 8.70 | 8.61 |
| Diclofenac K Assay (%) | 95.0-105.0 | 101.1 | 101.0 | 99.6 |
| Impurity 1 (%) RRT = 0.38 | NMT 0.2 | — | — | — |
| Impurity 2 (%) RRT = 0.44 | NMT 0.2 | — | — | — |
| Impurity A (3) (%) RRT = 0.60 | NMT 0.2 | — | — | — |
| Impurity C (4) (%) RRT = 0.82 | NMT 0.2 | 0.150 | 0.185 | 0.163 |
| Impurity B (6) (%) RRT = 1.39 | NMT 0.2 | — | — | — |
| Impurity 5 (%) RRT = 1.12 | NMT 0.2 | — | — | 0.101 |
| Total (known and unknown) impurities (%) | NMT 1.0 | 0.150 | 0.185 | 0.264 |

Example 17 Liquid Oral Solution with Diclofenac and High Quantity of Sorbitol, with Sucralose (Prototype PFS DK 26A-bkT038/71)

The following formulation has been prepared to obtain a ready to use liquid solution containing 50 mg of Diclofenac in 20 g of formula. Differently from Example 1, Sucralose is added to Non crystallizing Sorbitol Solution; the preparation is carried out under nitrogen.

Quail/Quantitative Formulation

| | Ingredient | mg/stick pack | % | g/bulk (500 g) |
|---|---|---|---|---|
| 1 | Diclofenac K | 50 | 0.25 | 1.25 |
| 2 | Potassium Bicarbonate (KHCO3) | 22 | 0.11 | 0.55 |
| 3 | Sucralose | 12 | 0.06 | 0.30 |
| 4 | Non crystallizing Sorbitol Solution | 19916 | 99.58 | 497.90 |
| | Total | 20000 | 100 | 500.0 |

Manufacturing Method
- Transfer the total quantity of Non crystallizing Sorbitol Solution in a glass container; treat the solution with nitrogen flow for about 30 minutes;
- Add Sucralose and Potassium Bicarbonate and wait for the complete dissolution (about 5 minutes); maintain the system under stirring and under nitrogen flow;
- Add Diclofenac Potassium and wait at least 2 hours maintaining the system under stirring and under nitrogen flow for all the time;
- Filter the solution;
- Store the solution in the selected container;
- Treat the headspace of the container with nitrogen flow before close the container.

Analytical Evaluations

Stability data

| PFS DK 26A - bkT038/71 | Tentative specifications | Time zero | Time 3 months 40° C., 75% RH Stick Pack | Time 6 months 40° C., 75% RH Stick Pack |
|---|---|---|---|---|
| Appearance of the solution | Colourless clear solution | Complies | Pale yellow clear solution | Pale yellow clear solution |
| pH (on sample, as it is) | To be defined | 8.46 | 7.91 | 7.92 |
| Diclofenac K Assay (%) | 95.0-105.0 | 99.7 | 100.5 | 96.1 |
| Impurity 1 (%) RRT = 0.38 | NMT 0.2 | — | — | — |
| Impurity 2 (%) RRT = 0.44 | NMT 0.2 | | | |
| Impurity A (3) (%) RRT = 0.60 | NMT 0.2 | | | |
| Impurity C (4) (%) RRT = 0.82 | NMT 0.2 | | | |
| Impurity B (6) (%) RRT = 1.39 | NMT 0.2 | | | |
| Impurity 5 (%) RRT = 1.12 | NMT 0.2 | | | |
| Total (known and unknown) impurities (%) | NMT 1.0 | — | — | — |

Example 18 Liquid Oral Solution with Diclofenac and High Quantity of Sorbitol, with Sucralose—14 ml Volume (Prototype PFS DK 70-bkT038/149)

The following formulation has been prepared to obtain a ready to use liquid solution containing 50 mg of Diclofenac in, differently from Example 13, in 18.2 g of formula. The preparation is not carried out under nitrogen.

Quail/Quantitative Formulation

|   | Ingredient | mg/stick pack | % | g/bulk (1000 g) |
|---|---|---|---|---|
| 1 | Diclofenac K | 50 | 0.275 | 2.75 |
| 2 | Potassium Bicarbonate (KHCO3) | 22 | 0.121 | 1.21 |
| 3 | Sucralose | 6.0 | 0.033 | 0.33 |
| 4 | Non crystallizing Sorbitol Solution | 18122 | 99.57 | 995.7 |
|   | Total | 18200.0 | 100.0 | 1000.0 |

Manufacturing Method

Transfer the total quantity of Non crystallizing Sorbitol Solution in a glass container;

Add Sucralose and Potassium Bicarbonate and wait for the complete dissolution (about 5 minutes); maintain the system under stirring;

Add Diclofenac Potassium and wait at least 2 hours maintaining the system under stirring;

Filter the solution;

Store the solution in the selected container.

Analytical Evaluations

Example 19 Liquid Oral Solution with Diclofenac and High Quantity of Sorbitol, without Sucralose—14 ml Volume (Prototype PFS DK 77-bkT038/156)

The following formulation has been prepared to obtain a ready to use liquid solution containing 50 mg of Diclofenac in, differently from Example 1, 18.2 g of formula. Differently from Example 14, the formula does not contain Sucralose. The preparation is not carried out under nitrogen.

Quail/Quantitative Formulation

|   | Ingredient | mg/stick pack | % | g/bulk (1000 g) |
|---|---|---|---|---|
| 1 | Diclofenac K | 50 | 0.275 | 2.75 |
| 2 | Potassium Bicarbonate (KHCO3) | 22 | 0.121 | 1.21 |
| 3 | Non crystallizing Sorbitol Solution | 18128.0 | 99.6 | 996.04 |
|   | Total | 18200.0 | 100.0 | 1000.0 |

Manufacturing Method

Transfer the total quantity of Non crystallizing Sorbitol Solution in a glass container;

Add Potassium Bicarbonate and wait for the complete dissolution (about 5 minutes); maintain the system under stirring;

Add Diclofenac Potassium and wait at least 2 hours maintaining the system under stirring;

Filter the solution;

Store the solution in the selected container.

| | | | Stability data | | |
|---|---|---|---|---|---|
| PFS DK 70 - bkT038/149 | Tentative specifications | Time zero | Time 3 months 25° C., 60% RH Stick Pack | Time 3 months 30° C., 65% RH Stick Pack | Time 3 months 40° C., 75% RH Stick Pack |
| Appearance of the solution | Colourless clear solution | Complies | Complies | Complies | Slightly yellow clear solution |
| pH (on sample, as it is) | To be defined | 8.60 | 8.33 | 8.32 | 8.12 |
| Diclofenac K Assay (%) | 95.0-105.0 | 98.7 | 100.9 | 100.9 | 100.2 |
| Impurity 1 (%) RRT = 0.38 | NMT 0.2 | — | — | — | — |
| Impurity 2 (%) RRT = 0.44 | NMT 0.2 | — | — | — | — |
| Impurity A (3) (%) RRT = 0.60 | NMT 0.2 | — | — | — | — |
| Impurity C (4) (%) RRT = 0.82 | NMT 0.2 | 0.11 | — | — | — |
| Impurity B (6) (%) RRT = 1.39 | NMT 0.2 | — | — | — | — |
| Impurity 5 (%) RRT = 1.12 | NMT 0.2 | — | — | — | — |
| Total (known and unknown) impurities (%) | NMT 1.0 | 0.11 | — | — | — |

Analytical Evaluations

Stability data

| PFS DK 77 - bkT038/156 | Tentative specifications | Time zero | Time 6 months 40° C., 75% RH Stick Pack |
|---|---|---|---|
| Appearance of the solution | Colourless clear solution | Complies | Slightly yellow clear solution with orange reflections |
| pH (on sample, as it is) | To be defined | 8.53 | 8.01 |
| Diclofenac K Assay (%) | 95.0-105.0 | 99.3 | 99.0 |
| Impurity 1 (%) RRT = 0.38 | NMT 0.2 | — | — |
| Impurity 2 (%) RRT = 0.44 | NMT 0.2 | — | — |
| Impurity A (3) (%) RRT = 0.60 | NMT 0.2 | — | — |
| Impurity C (4) (%) RRT = 0.82 | NMT 0.2 | — | — |
| Impurity B (6) (%) RRT = 1.39 | NMT 0.2 | — | — |
| Impurity 5 (%) RRT = 1.12 | NMT 0.2 | — | — |
| Total (known and unknown) impurities (%) | NMT 1.0 | — | — |

Example 20 Liquid Oral Solution with Diclofenac and High Quantity of Sorbitol, with Polyvinylpyrrolidone—14 ml Volume, with and without Flavoring Agent (Prototype PFS DK 85-bkT038/168 and Prototype PFS DK 87-bkT038/170)

The following formulations have been prepared to obtain a ready to use liquid solution containing 50 mg of Diclofenac in 18.2 g of formula. The addition of PVP, with and without a flavoring agent, is here evaluated. The preparation is not carried out under nitrogen.

Quail/Quantitative Formulation

| | Ingredient | PFS DK 85-bkT038/168 mg/stick pack | PFS DK 87-bkT038/170 mg/stick pack | PFS DK 85-bkT038/168 % | PFS DK 87-bkT038/170 % | PFS DK 85-bkT038/168 g/bulk (1000 g) | PFS DK 87-bkT038/170 g/bulk (1000 g) |
|---|---|---|---|---|---|---|---|
| 1 | Diclofenac K | 50 | 50 | 0.275 | 0.275 | 2.747 | 2.747 |
| 2 | Potassium Bicarbonate (KHCO3) | 22 | 22 | 0.121 | 0.121 | 1.209 | 1.209 |
| 3 | Polyvinylpyrrolidone (PVP) | 80 | 80 | 0.4396 | 0.4396 | 4.396 | 4.396 |
| 4 | Non crystallizing Sorbitol Solution | 18015.2 | 18048.0 | 99.0 | 99.2 | 989.846 | 991.648 |
| 5 | Masking Bitter Flavor | 32.8 | — | 0.18 | — | 1.802 | — |
| | Total (mg) | 18200.0 | 18200.0 | 100.0 | 100.0 | 1000.0 | 1000.0 |

Manufacturing Method

Transfer the total quantity of Non crystallizing Sorbitol Solution in a glass container;

Add PVP and wait for the complete dissolution (about 5 minutes); maintain the system under stirring;

Add Potassium Bicarbonate and wait for the complete dissolution (about 5 minutes); maintain the system under stirring;

Add Diclofenac Potassium and wait at least 2 hours maintaining the system under stirring;

Filter the solution;

Add the flavor (for PFS DK 85)

Store the solution in the selected container.

Analytical Evaluations

Stability data (performed only on PFS DK 87-bkT038/170)

| PFS DK 87 - bkT038/170 | Tentative specifications | Time zero | Time 12 months 25° C., 60% RH Stick Pack | Time 6 months 30° C., 65% RH Stick Pack | Time 6 months 40° C., 75% RH Stick Pack |
|---|---|---|---|---|---|
| Appearance of the solution | Colourless clear solution | Complies | Complies | Complies | Pale yellow clear solution |
| pH (on sample, as it is) | To be defined | 8.40 | 8.06 | 8.38 | 8.15 |
| Diclofenac K Assay (%) | 95.0-105.0 | 99.5 | 97.3 | 101.2 | 99.4 |

Stability data (performed only on PFS DK 87-bkT038/170)

| PFS DK 87 - bkT038/170 | Tentative specifications | Time zero | Time 12 months 25° C., 60% RH Stick Pack | Time 6 months 30° C., 65% RH Stick Pack | Time 6 months 40° C., 75% RH Stick Pack |
|---|---|---|---|---|---|
| Impurity 1 (%) RRT = 0.38 | NMT 0.2 | — | — | — | 0.122 |
| Impurity 2 (%) RRT = 0.44 | NMT 0.2 | — | — | — | — |
| Impurity A (3) (%) RRT = 0.60 | NMT 0.2 | — | — | — | — |
| Impurity C (4) (%) RRT = 0.82 | NMT 0.2 | — | — | — | — |
| Impurity B (6) (%) RRT = 1.39 | NMT 0.2 | — | — | — | — |
| Impurity 5 (%) RRT = 1.12 | NMT 0.2 | — | — | — | — |
| Total (known and unknown) impurities (%) | NMT 1.0 | — | — | — | 0.122 |

Example 21 Liquid Oral Solution with Diclofenac and Medium Quantity of Sorbitol, with Polyvinylpyrrolidone and Hydroxyethylcellulose—14 ml Volume, with Flavoring Agent (Prototype PFS DK 86-bkT038/169)

The following formulation has been prepared to obtain a ready to use liquid solution containing 50 mg of Diclofenac in 18.2 g of formula. The addition of Hydroxyethylcellulose (HEC) and Polyvinylpyrrolidone (PVP), with a flavoring agent, is here evaluated. The preparation is not carried out under nitrogen.

Quali/Quantitative Formulation

| | Ingredient | mg/stick pack | % | g/bulk (100 g) |
|---|---|---|---|---|
| 1 | Diclofenac K | 50 | 0.275 | 2.755 |
| 2 | Potassium Bicarbonate (KHCO3) | 22 | 0.121 | 1.212 |
| 3 | Non crystallizing Sorbitol Solution | 14325 | 78.71 | 787.1 |
| 4 | Water | 3620 | 19.89 | 198.9 |
| 5 | Polyvinylpyrrolidone (PVP) | 100 | 0.55 | 5.5 |
| 6 | Hydroxyethyl cellulose (HEC) | 50 | 0.27 | 2.7 |
| 7 | Masking Bitter Flavor | 33 | 0.18 | 1.8 |
| | Total | 18200.0 | 100.0 | 1000.0 |

Manufacturing Method

Dissolve under stirring all the PVP, add the HEC in water and wait for the complete dissolution (about 3 hours);

Transfer the total quantity of Non crystallizing Sorbitol Solution in a glass container;

Add Potassium Bicarbonate and wait for the complete dissolution (about 5 minutes); maintain the system under stirring;

Add Diclofenac Potassium and wait at least 2 hours maintaining the system under stirring;

Mix the solutions obtained;

Add the flavor and mix for 5 minutes;

Store the solution in the selected container.

Analytical Evaluations

Stability data

| PFS DK 86 - bkT038/169 | Tentative specifications | Time zero | Time 3 months 25° C., 60% RH Stick Pack | Time 3 months 30° C., 65% RH Stick Pack | Time 3 months 40° C., 75% RH Stick Pack |
|---|---|---|---|---|---|
| Appearance of the solution | Colourless clear solution | Complies | Complies | Complies | Dark yellow clear solution |
| pH (on sample, as it is) | To be defined | 7.78 | 7.78 | 7.82 | 7.55 |
| Diclofenac K Assay (%) | 95.0-105.0 | 101.0 | 102.0 | 102.1 | 100.9 |
| Impurity 1 (%) RRT = 0.38 | NMT 0.2 | — | — | — | — |
| Impurity 2 (%) RRT = 0.44 | NMT 0.2 | — | — | — | — |
| Impurity A (3) (%) RRT = 0.60 | NMT 0.2 | — | — | — | — |
| Impurity C (4) (%) RRT = 0.82 | NMT 0.2 | — | — | — | — |
| Impurity B (6) (%) RRT = 1.39 | NMT 0.2 | — | — | — | — |
| Impurity 5 (%) RRT = 1.12 | NMT 0.2 | — | — | — | 0.385 |
| Total (known and unknown) impurities (%) | NMT 1.0 | — | — | — | 0.385 |

Example 22 Liquid Oral Solution with Diclofenac, Medium Quantity of Sorbitol, Erythritol and Sucralose, without Nitrogen (Prototype PFS DK 63-bkT038/140)

The following formulation has been prepared to obtain a ready to use liquid solution containing 50 mg of Diclofenac in 20 g of formula; sorbitol and erythritol are here mixed with sucralose and water to obtain the formula. The preparation is not carried out under nitrogen.

Quail/Quantitative Formulation

|   | Ingredient | mg/stick pack | % | g/bulk (100 g) |
|---|---|---|---|---|
| 1 | Diclofenac K | 50 | 0.25 | 0.25 |
| 2 | Potassium Bicarbonate (KHCO3) | 22 | 0.11 | 0.11 |
| 3 | Erythritol | 5000 | 25.00 | 25.00 |
| 4 | Non crystallizing Sorbitol Solution | 7142 | 35.71 | 35.71 |
| 5 | Water | 7774 | 38.87 | 38.87 |
| 6 | Sucralose | 12 | 0.06 | 0.06 |
|   | Total (mg) | 20000 | 100 | 100 |

Manufacturing Method

Transfer the total quantity of Non crystallizing Sorbitol Solution, Erythritol and water in a glass container;
Add Sucralose and Potassium Bicarbonate and wait for the complete dissolution (about 5 minutes); maintain the system under stirring;
Add Diclofenac Potassium and wait at least 2 hours maintaining the system under stirring;
Filter the solution;
Store the solution in the selected container.

Example 23 Liquid Oral Solution with Diclofenac Sorbitol and Glycerin without Nitrogen (Prototype PFS DK 91-bkT038/176)

The following formulations have been prepared to obtain a ready to use liquid solution containing 50 mg of Diclofenac in 16 g of formula; Sorbitol and Glycerin are here mixed to obtain the formula. The preparation is not carried out under nitrogen.

Quail/Quantitative Formulation

|   | Ingredient | mg/stick pack | % | g/bulk (1000 g) |
|---|---|---|---|---|
| 1 | Diclofenac K | 50 | 0.31 | 3.13 |
| 2 | Potassium Bicarbonate (KHCO3) | 22 | 0.14 | 1.38 |
| 3 | Non crystallizing Sorbitol Solution | 7142 | 44.64 | 446.38 |
| 4 | Glycerin | 6400 | 40.00 | 400.00 |
| 5 | Water | 2207 | 13.79 | 137.94 |
| 6 | Plasdone K29/32 | 100 | 0.63 | 6.25 |
| 7 | Hydroxyethyl cellulose | 50 | 0.31 | 3.13 |
| 8 | Masking Bitter Flavor | 29 | 0.18 | 1.81 |
|   | Total (mg) | 16000 | 100.00 | 1000.00 |

Manufacturing Method

Transfer the total quantity of Non crystallizing Sorbitol Solution, Glycerin, Potassium Bicarbonate and Diclofenac in a glass container and stir until complete dissolution;
Transfer the total quantity of water in a glass container and dissolve the Plasdone K29/32 and the Hydroxyethyl cellulose;
Mix the two preparations obtained as above described and stir until a homogeneous solution is obtained;
Add the flavor maintaining the system under stirring;
Filter the solution;
Store the solution in the selected container.

Analytical Evaluations

| | | Stability data | | | |
|---|---|---|---|---|---|
| PFS DK 91 - bkT038/176 | Tentative specifications | Time zero | Time 3 months 25° C., 60% RH Stick Pack | Time 3 months 30° C., 65% RH Stick Pack | Time 3 months 40° C., 75% RH Stick Pack |
| Appearance of the solution | Colourless clear solution | Complies | Complies | Complies | Complies |
| pH (on sample, as it is) | To be defined | 8.05 | 8.46 | 8.39 | 8.17 |
| Diclofenac K Assay (%) | 95.0-105.0 | 100.4 | 99.8 | 99.7 | 99.3 |
| Impurity 1 (%) RRT = 0.38 | NMT 0.2 | — | — | — | — |
| Impurity 2 (%) RRT = 0.44 | NMT 0.2 | — | — | — | — |
| Impurity A (3) (%) RRT = 0.60 | NMT 0.2 | — | — | — | — |
| Impurity C (4) (%) RRT = 0.82 | NMT 0.2 | — | — | — | — |
| Impurity B (6) (%) RRT = 1.39 | NMT 0.2 | — | — | — | — |
| Impurity 5 (%) RRT = 1.12 | NMT 0.2 | — | — | — | 0.234 |
| Total (known and unknown) impurities (%) | NMT 1.0 | — | — | — | 0.234 |

Example 24 Liquid Oral Solution with Diclofenac, Sorbitol and Glycerin without Nitrogen (Prototype PFS DK 92-bkT038/178)

The following formulations have been prepared to obtain a ready to use liquid solution containing 50 mg of Diclofenac in 16 g of formula; Sorbitol and Glycerin are here mixed to obtain the formula, in a different ratio in comparison to Example 23. The preparation is not carried out under nitrogen.

Quali/Quantitative Formulation

|   | Ingredient | mg/stick pack | % | g/bulk (1000 g) |
|---|---|---|---|---|
| 1 | Diclofenac K | 50 | 0.31 | 3.13 |
| 2 | Potassium Bicarbonate (KHCO3) | 22 | 0.14 | 1.38 |
| 3 | Non crystallizing Sorbitol Solution | 5000 | 31.25 | 312.50 |
| 4 | Glycerin | 8400 | 52.50 | 525.00 |
| 5 | Water | 2349 | 14.68 | 146.81 |
| 6 | Plasdone K29/32 | 100 | 0.63 | 6.25 |
| 7 | Hydroxyethyl cellulose | 50 | 0.31 | 3.13 |
| 8 | Bitter Masking | 29 | 0.18 | 1.81 |
|   | Total (mg) | 16000 | 100.00 | 1000.00 |

Manufacturing Method

Transfer the total quantity of Non crystallizing Sorbitol Solution, Glycerin, Potassium Bicarbonate and Diclofenac in a glass container and stir until complete dissolution;

Transfer the total quantity of water in a glass container and dissolve the Plasdone K29/32 and the Hydroxyethylcellulose;

Mix the two preparations obtained as above described and stir until a homogeneous solution is obtained;

Add the Bitter masking maintaining the system under stirring;

Filter the solution;

Store the solution in the selected container

Analytical Evaluations

Example 25 Liquid Oral Solution with Diclofenac Sorbitol and Maltitol, without Nitrogen (Prototype PFS DK 93-bkT038/180)

The following formulations have been prepared to obtain a ready to use liquid solution containing 50 mg of Diclofenac in 16 g of formula; Sorbitol and Maltitol are here mixed to obtain the formula. The preparation is not carried out under nitrogen.

Quali/Quantitative Formulation

|   | Ingredient | mg/stick pack | % | g/bulk (1000 g) |
|---|---|---|---|---|
| 1 | Diclofenac K | 50 | 0.31 | 3.13 |
| 2 | Potassium Bicarbonate (KHCO3) | 22 | 0.14 | 1.38 |
| 3 | Non crystallizing Sorbitol Solution | 5000 | 31.25 | 312.50 |
| 4 | Maltitol syrup 75% | 8400 | 52.50 | 525.00 |
| 5 | Water | 2349 | 14.68 | 146.81 |
| 6 | Plasdone K29/32 | 100 | 0.63 | 6.25 |
| 7 | Hydroxyethyl cellulose | 50 | 0.31 | 3.13 |
| 8 | Masking Bitter Flavor | 29 | 0.18 | 1.81 |
|   | Total (mg) | 16000 | 100.00 | 1000.00 |

Manufacturing Method

Transfer the total quantity of Non crystallizing Sorbitol Solution, Maltitol, Potassium Bicarbonate and Diclofenac in a glass container and stir until complete dissolution;

Add the half part of hydroxyethylcellulose and stir until complete dissolution;

Transfer the total quantity of water in a glass container and dissolve the Plasdone K29/32 and the half part of hydroxyethylcellulose;

Mix the two preparations obtained as above described and stir until a homogeneous solution is obtained;

Add the flavor maintaining the system under stirring;

Filter the solution;

Store the solution in the selected container.

Stability data

| PFS DK 92 - bkT038/178 | Tentative specifications | Time zero | Time 3 months 25° C., 60% RH Stick Pack | Time 3 months 30° C., 65% RH Stick Pack | Time 3 months 40° C., 75% RH Stick Pack |
|---|---|---|---|---|---|
| Appearance of the solution | Colourless clear solution | Complies | Complies | Complies | Complies |
| pH (on sample, as it is) | To be defined | 8.22 | 8.39 | 8.41 | 8.02 |
| Diclofenac K Assay (%) | 95.0-105.0 | 98.7 | 99.8 | 100.0 | 99.0 |
| Impurity 1 (%) RRT = 0.38 | NMT 0.2 | — | — | — | — |
| Impurity 2 (%) RRT = 0.44 | NMT 0.2 | — | — | — | — |
| Impurity A (3) (%) RRT = 0.60 | NMT 0.2 | — | — | — | — |
| Impurity C (4) (%) RRT = 0.82 | NMT 0.2 | — | — | — | — |
| Impurity B (6) (%) RRT = 1.39 | NMT 0.2 | — | — | — | — |
| Impurity 5 (%) RRT = 1.12 | NMT 0.2 | — | — | — | 0.136 |
| Total (known and unknown) impurities (%) | NMT 1.0 | — | — | — | 0.136 |

Analytical Evaluations

| PFS DK 93 - bkT038/180 | Tentative specifications | Time zero | Time 3 months 25° C., 60% RH Stick Pack | Time 3 months 30° C., 65% RH Stick Pack | Time 3 months 40° C., 75% RH Stick Pack |
|---|---|---|---|---|---|
| Stability data | | | | | |
| Appearance of the solution | Colourless clear solution | Complies | Complies | Complies | Complies |
| pH (on sample, as it is) | To be defined | 8.36 | 8.23 | 8.24 | 8.21 |
| Diclofenac K Assay (%) | 95.0-105.0 | 105.3 | 104.6 | 104.5 | 104.0 |
| Impurity 1 (%) RRT = 0.38 | NMT 0.2 | — | — | — | — |
| Impurity 2 (%) RRT = 0.44 | NMT 0.2 | — | — | — | — |
| Impurity A (3) (%) RRT = 0.60 | NMT 0.2 | — | — | — | — |
| Impurity C (4) (%) RRT = 0.82 | NMT 0.2 | — | — | — | — |
| Impurity B (6) (%) RRT = 1.39 | NMT 0.2 | — | — | — | — |
| Impurity 5 (%) RRT = 1.12 | NMT 0.2 | — | — | — | 0.185 |
| Total (known and unknown) impurities (%) | NMT 1.0 | — | — | — | 0.185 |

Example 26 Liquid Oral Solution with Diclofenac Sorbitol and Maltitol, without Nitrogen (Prototype PFS DK 96-bkT038/187)

The following formulations have been prepared to obtain a ready to use liquid solution containing 50 mg of Diclofenac in 16 g of formula; Sorbitol and Fructose are here mixed with thickening agents to obtain the formula. The preparation is not carried out under nitrogen.

Quail/Quantitative Formulation

|   | Ingredient | mg/stick pack | % | g/bulk (1000 g) |
|---|---|---|---|---|
| 1 | Diclofenac K | 50 | 0.31 | 3.13 |
| 2 | Potassium Bicarbonate (KHCO3) | 22 | 0.14 | 1.38 |
| 3 | Non crystallizing Sorbitol Solution | 11420 | 71.38 | 713.75 |
| 4 | Plasdone K29/32 | 100 | 0.63 | 6.25 |
| 5 | Fructose | 2400 | 15.00 | 150.00 |
| 6 | Water | 1929 | 12.06 | 120.56 |
| 7 | Hydroxyethyl cellulose | 50 | 0.31 | 3.13 |
| 8 | Masking Bitter Flavor | 29 | 0.18 | 1.81 |
|   | Total (mg) | 16000.0 | 100.0 | 1000.0 |

Manufacturing Method

Transfer the total quantity of Non crystallizing Sorbitol Solution, Fructose, Potassium Bicarbonate and Diclofenac in a glass container and stir until complete dissolution;

Add the half part of hydroxyethylcellulose and stir until complete dissolution;

Transfer the total quantity of water in a glass container and dissolve the Plasdone K29/32 and the half part of hydroxyethylcellulose;

Mix the two preparations obtained as above described and stir until a homogeneous solution is obtained;

Add the flavor maintaining the system under stirring;

Filter the solution;

Store the solution in the selected container.

Example 27 Liquid Oral Solution with Diclofenac and Sorbitol, without Nitrogen, Under Vacuum Conditions (Prototype PFS DK 119-bkT038/211)

The following formulation has been prepared to obtain a ready to use liquid solution containing 50 mg of Diclofenac in 12.9 g of formula; Sorbitol is here mixed with Polyvinylpyrrolidone as a thickening agent to obtain the formula. The preparation is carried out with laboratory equipment in a higher batch size compared with the previous batches, not under nitrogen but under vacuum conditions.

Quail/Quantitative Formulation

|   | Ingredient | mg/stick pack | % | g/bulk (2500 g) |
|---|---|---|---|---|
| 1 | Diclofenac K | 50.0 | 0.39 | 9.69 |
| 2 | Potassium Bicarbonate (KHCO3) | 22.0 | 0.17 | 4.26 |
| 3 | Non crystallizing Sorbitol Solution | 12757.20 | 98.89 | 2472.33 |
| 4 | Plasdone K29/32 | 70.80 | 0.55 | 13.72 |
|   | Total | 12900.00 | 100.00 | 2500.00 |

Manufacturing Method

Transfer the total quantity of Non crystallizing Sorbitol Solution, in the mixer tank, under vacuum conditions;

Add all the Plasdone K29/32 and mix at regular intervals until a homogeneous solution is obtained, maintaining the apparatus under vacuum conditions;

Add Potassium Bicarbonate and Diclofenac, mix at regular intervals until a homogeneous solution is obtained, maintaining the apparatus under vacuum conditions;

Store the solution in the selected container.

Example 28 Liquid Oral Solution with Diclofenac, Sorbitol and Flavoring Agent, without Nitrogen, Under Vacuum Conditions (Prototype PFS DK 120-bkT038/212)

The following formulation has been prepared to obtain a ready to use liquid solution containing 50 mg of Diclofenac in 12.9 g of formula; Sorbitol is here mixed with Polyvinylpyrrolidone as thickening agent and bitter masking as flavoring agent to obtain the formula. The preparation is obtained by the addition of the flavoring agent to Prototype PFS DK 119.

Quail/Quantitative Formulation

|   | Ingredient | mg/stick pack | % | g/bulk (500 g) |
|---|---|---|---|---|
| 1 | Diclofenac K | 50 | 0.39 | 1.94 |
| 2 | Potassium Hydrogen Carbonate | 22 | 0.17 | 0.85 |
| 3 | Non crystallizing Sorbitol Solution | 12734.2 | 98.71 | 493.57 |
| 4 | Plasdone K29/32 | 70.8 | 0.55 | 2.74 |
| 5 | Masking Bitter Flavor | 23 | 0.18 | 0.89 |
|   | Total (mg) | 12900.00 | 100.00 | 500.00 |

Manufacturing Method
The bitter masking is added on a fraction of the prototype PFS DK 119 and mixed until a homogeneous solution is obtained;
Store the solution in the selected container.

Example 29 Liquid Oral Solution with Diclofenac, Sorbitol and Glycerin, without Nitrogen, Under Vacuum Conditions (Prototype PFS DK 121-bkT038/213)

The following formulation has been prepared to obtain a ready to use liquid solution containing 50 mg of Diclofenac in 12.2 g of formula; Sorbitol and Glycerin are here mixed with Polyvinylpyrrolidone as thickening agent to obtain the formula. The preparation is carried out with a laboratory equipment, in a higher batch size compared with the previous batches, not under nitrogen but under vacuum conditions.
Quail/Quantitative Formulation

|   | Ingredient | mg/stick pack | % | g/bulk (2500 g) |
|---|---|---|---|---|
| 1 | Diclofenac K | 50 | 0.41 | 10.23 |
| 2 | Potassium Hydrogen Carbonate | 22 | 0.18 | 4.50 |
| 3 | Non crystallizing Sorbitol Solution | 4529 | 37.06 | 926.55 |
| 4 | Glycerin | 7548 | 61.77 | 1544.19 |
| 5 | Plasdone K29/32 | 71 | 0.58 | 14.53 |
|   | Total (mg) | 12220 | 100.00 | 2500.00 |

Manufacturing Method
Transfer the total quantity of Glycerin, in the mixer tank, under vacuum conditions;
Add all the Plasdone K29/32 and mix at regular intervals until a homogeneous solution is obtained, maintaining the apparatus under vacuum conditions;
Add the total quantity of Non crystallizing Sorbitol Solution
Add Potassium Bicarbonate and Diclofenac, mix at regular intervals until a homogeneous solution is obtained, maintaining the apparatus under vacuum conditions;
Store the solution in the selected container.

Example 30 Liquid Oral Solution with Diclofenac, Sorbitol, Glycerin and Flavoring Agent, without Nitrogen, Under Vacuum Conditions (Prototype PFS DK 122-bkT038/214)

The following formulation has been prepared to obtain a ready to use liquid solution containing 50 mg of Diclofenac in 12.2 g of formula; Sorbitol and Glycerin are here mixed with Polyvinylpyrrolidone as thickening agent and bitter masking as flavoring agent to obtain the formula. The preparation is obtained by the addition of the flavoring agent to Prototype PFS DK 121.
Quail/Quantitative Formulation

|   | Ingredient | mg/stick pack | % | g/bulk (500 g) |
|---|---|---|---|---|
| 1 | Diclofenac K | 50 | 0.41 | 2.05 |
| 2 | Potassium Hydrogen Carbonate | 22 | 0.18 | 0.90 |
| 3 | Non crystallizing Sorbitol Solution | 4520 | 36.99 | 184.94 |
| 4 | Glycerin | 7535 | 61.66 | 308.31 |
| 5 | Plasdone K29/32 | 71 | 0.58 | 2.91 |
| 6 | Masking Bitter Flavor | 22 | 0.18 | 0.90 |
|   | Total (mg) | 12220 | 100.00 | 500.00 |

Manufacturing Method
The bitter masking is added on a fraction of the prototype PFS DK 121 and mixed until a homogeneous solution is obtained;
Store the solution in the selected container.

Example 31 Liquid Oral Solution with Diclofenac, Sorbitol and Maltitol, without Nitrogen, Under Vacuum Conditions (Prototype PFS DK 123-bkT038/215)

The following formulation has been prepared to obtain a ready to use liquid solution containing 50 mg of Diclofenac in 12.9 g of formula; Sorbitol and Maltitol are here mixed with Polyvinylpyrrolidone as thickening agent. The preparation is carried out with a laboratory equipment, in a higher batch size compared with the previous batches, not under nitrogen but under vacuum conditions.
Quail/Quantitative Formulation

|   | Ingredient | mg/stick pack | % | g/bulk (2500 g) |
|---|---|---|---|---|
| 1 | Diclofenac K | 50 | 0.39 | 9.69 |
| 2 | Potassium Hydrogen Carbonate | 22 | 0.17 | 4.26 |
| 3 | Non crystallizing Sorbitol Solution | 4784 | 37.09 | 927.13 |
| 4 | Maltitol Syrup | 7973 | 61.81 | 1545.16 |
| 5 | Plasdone K29/32 | 71 | 0.55 | 13.76 |
|   | Total | 12900 | 100.00 | 2500.00 |

Manufacturing Method
Transfer the total quantity of Maltitol, in the mixer tank, under vacuum conditions;
Add all the Plasdone K29/32 and mix at regular intervals until a homogeneous solution is obtained, maintaining the apparatus under vacuum conditions;
Add the total quantity of Non crystallizing Sorbitol Solution
Add Potassium Bicarbonate and Diclofenac, mix at regular intervals until a homogeneous solution is obtained, maintaining the apparatus under vacuum conditions;
Store the solution in the selected container.

Example 32 Liquid Oral Solution with Diclofenac, Sorbitol, Maltitol and Flavoring Agent, without Nitrogen, Under Vacuum Conditions (Prototype PFS DK 124-bkT038/216)

The following formulation has been prepared to obtain a ready to use liquid solution containing 50 mg of Diclofenac in 12.9 g of formula; Sorbitol and Maltitol are here mixed with Polyvinylpyrrolidone as thickening agent and bitter masking as flavoring agent to obtain the formula. The preparation is obtained by the addition of the flavoring agent to Prototype PFS DK 123.

Quali/Quantitative Formulation

|   | Ingredient | mg/stick pack | % | g/bulk (500 g) |
|---|---|---|---|---|
| 1 | Diclofenac K | 50 | 0.39 | 1.94 |
| 2 | Potassium Hydrogen Carbonate | 22 | 0.17 | 0.85 |
| 3 | Non crystallizing Sorbitol Solution | 4775 | 37.02 | 185.08 |
| 4 | Maltitol Syrup | 7959 | 61.70 | 308.49 |
| 5 | Plasdone K29/32 | 71 | 0.55 | 2.75 |
| 6 | Masking Bitter Flavor | 23 | 0.18 | 0.89 |
|   | Total | 12900 | 100.00 | 500.00 |

Manufacturing Method

The bitter masking is added on a fraction of the prototype PFS DK 123 and mixed until a homogeneous solution is obtained;

Store the solution in the selected container.

Example 33 Liquid Oral Solution with Diclofenac and Sorbitol, without Nitrogen, with and without Flavoring Agent (Prototype PFS DK 125-bkT038/217 and Prototype PFS DK 126-bkT038/218)

The following formulations have been prepared to obtain a ready to use liquid solution containing 50 mg of Diclofenac in 12.3 g of formula; the addition of Polyvinylpyrrolidone and Hydroxyethylcellulose to the formula, with and without a flavouring agent, is here evaluated. The preparation is not carried out under nitrogen.

|   | Ingredient | PFS DK 125-bkT038/217 mg/stick pack | PFS DK 126-bkT038/218 mg/stick pack | PFS DK 125-bkT038/217 g/bulk (500 g) | PFS DK 126-bkT038/218 g/bulk (500 g) |
|---|---|---|---|---|---|
| 1 | Diclofenac K | 50.00 | 50.00 | 2.050 | 2.050 |
| 2 | Potassium Hydrogen Carbonate | 22.00 | 22.00 | 0.900 | 0.900 |
| 3 | Purified water | 1803.00 | 1803.00 | 73.300 | 73.300 |
| 4 | Non crystallizing Sorbitol Solution | 10332.00 | 10310.00 | 420.000 | 419.100 |
| 5 | Plasdone K29/32 | 54.00 | 54.00 | 2.200 | 2.200 |
| 6 | Hydroxyethyl cellulose | 38.00 | 38.00 | 1.550 | 1.550 |
| 7 | Masking Bitter Flavor | — | 22.00 | — | 0.900 |
|   | Total (mg) | 12299.00 | 12299.0 | 500.0 | 500.0 |

Example 34 Liquid Oral Solution with Diclofenac and Sorbitol, without Nitrogen, with and without Flavoring Agent (Prototype PFS DK 127-bkT038/219 and Prototype PFS DK 128-bkT038/220)

The following formulations have been prepared to obtain a ready to use liquid solution containing 50 mg of Diclofenac in 17.2 g of formula; the addition of Polyvinylpyrrolidone and Hydroxyethylcellulose to the formula, with and without a flavouring agent, is here evaluated. The preparation is not carried out under nitrogen.

| Ingredient | PFS DK 127-bkT038/219 mg/stick pack | PFS DK 128-bkT038/220 mg/stick pack | PFS DK 127-bkT038/219 g/bulk (500 g) | PFS DK 128-bkT038/220 g/bulk (500 g) |
|---|---|---|---|---|
| Diclofenac K | 50.00 | 50.00 | 1.550 | 1.550 |
| Potassium Hydrogen Carbonate | 22.00 | 22.00 | 0.700 | 0.700 |
| Purified water | 2609.00 | 2578.00 | 73.300 | 73.300 |
| Non crystallizing Sorbitol Solution | 14410.00 | 14410.00 | 420.700 | 419.800 |
| Plasdone K29/32 | 76.00 | 76.00 | 2.200 | 2.200 |
| Hydroxy ethyl cellulose | 53.00 | 53.00 | 1.550 | 1.550 |
| Masking Bitter Flavor | — | 31.000 | — | 0.900 |
| Total (mg) | 17220.00 | 17220.00 | 500.0 | 500.0 |

Example 35 Liquid Oral Solution with Diclofenac, Sorbitol and Glycerin, without Nitrogen, with and without Flavoring Agent (Prototype PFS DK 129-bkT038/221 and Prototype PFS DK 130-bkT038/222)

The following formulations have been prepared to obtain a ready to use liquid solution containing 50 mg of Diclofenac in 12.3 g of formula; Sorbitol and Glycerin are here mixed with Polyvinylpyrrolidone and Hydroxyethylcellulose to obtain the formula, with and without a flavouring agent. The preparation is not carried out under nitrogen.

| | Ingredient | PFS DK 129-bkT038/221 | PFS DK 130-bkT038/222 | PFS DK 129-bkT038/221 | PFS DK 130-bkT038/222 |
| | | mg/stick pack | | g/bulk (500 g) | |
|---|---|---|---|---|---|
| 1 | Diclofenac K | 50.00 | 50.00 | 2.050 | 2.050 |
| 2 | Potassium Hydrogen Carbonate | 22.00 | 22.00 | 0.900 | 0.900 |
| 3 | Purified water | 1806.00 | 1806.00 | 73.400 | 73.400 |
| 4 | Non crystallizing Sorbitol Solution | 3844.00 | 3844.00 | 156.250 | 156.250 |
| 5 | Glycerin | 6462.00 | 6440.00 | 262.700 | 261.800 |
| 6 | Plasdone K29/32 | 77.00 | 77.00 | 3.150 | 3.150 |
| 7 | Hydroxyethyl cellulose | 38.00 | 38.00 | 1.550 | 1.550 |
| 8 | Masking Bitter Flavor | — | 22.00 | — | 0.900 |
| | Total (mg) | 12299.00 | 12299.00 | 500.0 | 500.0 |

Example 36 Liquid Oral Solution with Diclofenac, Sorbitol and Glycerin, without Nitrogen, with and without Flavoring Agent (Prototype PFS DK 131-bkT038/223 and Prototype PFS DK 132-bkT038/224)

The following formulations have been prepared to obtain a ready to use liquid solution containing 50 mg of Diclofenac in 16.1 g of formula; Sorbitol and Glycerin are here mixed with Plasdone and Hydroxyethylcellulose to obtain the formula, with and without a flavouring agent. The preparation is not carried out under nitrogen.

| | Ingredient | PFS DK 131-bkT038/223 | PFS DK 132-bkT038/224 | PFS DK 131-bkT038/223 | PFS DK 132-bkT038/224 |
| | | mg/stick pack | | g/bulk (500 g) | |
|---|---|---|---|---|---|
| 1 | Diclofenac K | 50.00 | 50.00 | 1.550 | 1.550 |
| 2 | Potassium Hydrogen Carbonate | 22.00 | 22.00 | 0.700 | 0.700 |
| 3 | Purified water | 2363.00 | 2363.00 | 73.400 | 73.400 |
| 4 | Non crystallizing Sorbitol Solution | 5031.00 | 5009.00 | 156.250 | 156.250 |
| 5 | Glycerin | 8481.00 | 8481.00 | 263.400 | 262.500 |
| 6 | Plasdone K29/32 | 101.00 | 101.00 | 3.150 | 3.150 |
| 7 | Hydroxyethyl cellulose | 50.00 | 50.00 | 1.550 | 1.550 |
| 8 | Masking Bitter Flavor | — | 22.00 | — | 0.900 |
| | Total (mg) | 16098.00 | 16098.00 | 500.0 | 500.0 |

Example 37 Liquid Oral Solution with Diclofenac, Sorbitol and Maltitol, without Nitrogen, with and without Flavoring Agent (Prototype PFS DK 133-bkT038/225 and Prototype PFS DK 134-bkT038/226)

The following formulations have been prepared to obtain a ready to use liquid solution containing 50 mg of Diclofenac in 12.2 g of formula; Sorbitol and Maltitol are here mixed with Polyvinylpyrrolidone and Hydroxyethylcellulose to obtain the formula, with and without a flavouring agent. The preparation is not carried out under nitrogen.

|   | Ingredient | PFS DK 133-bkT038/225 mg/stick pack | PFS DK 134-bkT038/226 mg/stick pack | PFS DK 133-bkT038/225 g/bulk (500 g) | PFS DK 134-bkT038/226 g/bulk (500 g) |
|---|---|---|---|---|---|
| 1 | Diclofenac K | 50.00 | 50.00 | 2.050 | 2.050 |
| 2 | Potassium Hydrogen Carbonate | 22.00 | 22.00 | 0.900 | 0.900 |
| 3 | Purified water | 1791.00 | 1791.00 | 73.400 | 73.400 |
| 4 | Non crystallizing Sorbitol Solution | 3812.50 | 3812.50 | 156.250 | 156.250 |
| 5 | Maltitol syrup 75% | 6409.90 | 6387.90 | 262.700 | 261.800 |
| 6 | Plasdone K29/32 | 76.90 | 76.90 | 3.150 | 3.150 |
| 7 | Hydroxyethyl cellulose | 37.80 | 37.80 | 1.550 | 1.550 |
| 8 | Masking Bitter Flavor | — | 22.00 | — | 0.900 |
|   | Total (mg) | 12200.00 | 12200.00 | 500.0 | 500.0 |

Example 38 Liquid Oral Solution with Diclofenac, Sorbitol and Maltitol, without Nitrogen, with and without Flavoring Agent (Prototype PFS DK 135-bkT038/227 and Prototype PFS DK 136-bkT038/228)

The following formulations have been prepared to obtain a ready to use liquid solution containing 50 mg of Diclofenac in about 16.1 g of formula; Sorbitol and Maltitol are here mixed with Polyvinylpyrrolidone and Hydroxyethylcellulose to obtain the formula, with and without a flavouring agent. The preparation is not carried out under nitrogen.

|   | Ingredient | PFS DK 135-bkT038/227 mg/stick pack | PFS DK 136-bkT038/228 mg/stick pack | PFS DK 135-bkT038/227 g/bulk (500 g) | PFS DK 136-bkT038/228 g/bulk (500 g) |
|---|---|---|---|---|---|
| 1 | Diclofenac K | 50.00 | 50.00 | 1.553 | 1.553 |
| 2 | Potassium Hydrogen Carbonate | 22.00 | 22.00 | 0.683 | 0.683 |
| 3 | Purified water | 2363.00 | 2363.00 | 73.394 | 73.394 |
| 4 | Non crystallizing Sorbitol Solution | 5031.00 | 5031.00 | 156.262 | 156.262 |
| 5 | Maltitol syrup 75% | 8481.00 | 8448.0 | 263.418 | 262.393 |
| 6 | Plasdone K29/32 | 101.00 | 101.00 | 3.137 | 3.137 |
| 7 | Hydroxyethyl cellulose | 50.00 | 50.00 | 1.553 | 1.025 |
| 8 | Masking Bitter Flavor | — | 33.00 | — | 1.553 |
|   | Total (mg) | 16100.0 | 16100.0 | 500.0 | 500.0 |

Example 39 Liquid Oral Solution with Diclofenac and High Quantity of Sorbitol as Crystallizing Sorbitol Solution, without Nitrogen (Prototype PFS DK 155-bkT038/270)

The following formulation has been prepared to obtain a ready to use liquid solution containing 50 mg of Diclofenac in 20 g of formula. The preparation is carried out as done for the PFS DK 34 (see Example 5) but using the Crystallizing Sorbitol Solution instead the Noncrystallizing one.

Quail/Quantitative Formulation

|   | Ingredient | mg/stick pack | % | g/bulk (500 g) |
|---|---|---|---|---|
| 1 | Diclofenac K | 50.00 | 0.25 | 1.25 |
| 2 | Potassium Bicarbonate (KHCO3) | 22.00 | 0.11 | 0.55 |
| 3 | Crystallizing Sorbitol Solution | 19928.00 | 99.64 | 498.20 |
|   | Total | 20000.00 | 100.00 | 500.00 |

Manufacturing Method
Transfer the total quantity of Crystallizing Sorbitol Solution in a glass container;
Add Potassium Bicarbonate and wait for the complete dissolution (about 5 minutes); maintain the system under stirring;
Add Diclofenac Potassium and wait at least 2 hours maintaining the system under stirring;
Filter the solution;
Store the solution in the selected container.

Example 40 Liquid Oral Solution with Diclofenac and Medium Quantity of Sorbitol as Crystallizing Sorbitol Solution, without Nitrogen (Prototype PFS DK 152-bkT038/266)

The following formulation has been prepared to obtain a ready to use liquid solution containing 50 mg of Diclofenac in 20 g of formula. The preparation is carried out as done for the PFS DK 42 (see Example 6) but using the Crystallizing Sorbitol Solution instead the Noncrystallizing one.
Quali/Quantitative Formulation

|   | Ingredient | mg/stick pack | % | g/bulk (500 g) |
|---|---|---|---|---|
| 1 | Diclofenac K | 50.00 | 0.25 | 1.25 |
| 2 | Potassium Bicarbonate (KHCO3) | 22.00 | 0.11 | 0.55 |
| 3 | Crystallizing Sorbitol Solution | 14286.00 | 71.43 | 357.15 |
| 4 | Water | 5642.00 | 28.21 | 141.05 |
|   | Total | 20000.00 | 100.00 | 500.00 |

Manufacturing Method
Transfer the total quantity of water and Crystallizing Sorbitol Solution in a glass container;
Add Potassium Bicarbonate and wait for the complete dissolution (about 5 minutes); maintain the system under stirring;
Add Diclofenac Potassium and wait at least 2 hours maintaining the system under stirring;
Filter the solution;
Store the solution in the selected container.

Example 41 Liquid Oral Solution with Diclofenac and Low Quantity of Sorbitol as Crystallizing Sorbitol Solution, without Nitrogen (Prototype PFS DK 151-bkT038/265)

The following formulation has been prepared to obtain a ready to use liquid solution containing 50 mg of Diclofenac in 20 g of formula. The preparation is carried out as done for the PFS DK 41 (see Example 7) but using the Crystallizing Sorbitol Solution instead of the non-crystallizing one.
Quail/Quantitative Formulation

|   | Ingredient | mg/stick pack | % | g/bulk (500 g) |
|---|---|---|---|---|
| 1 | Diclofenac K | 50.00 | 0.25 | 1.25 |
| 2 | Potassium Bicarbonate (KHCO3) | 22.00 | 0.11 | 0.55 |
| 3 | Crystallizing Sorbitol Solution | 7122.00 | 35.61 | 178.05 |
| 4 | Water | 12806.00 | 64.03 | 320.15 |
|   | Total | 20000.00 | 100.00 | 500.00 |

Manufacturing Method
Transfer the total quantity of water and Crystallizing Sorbitol Solution in a glass container;
Add Potassium Bicarbonate and wait for the complete dissolution (about 5 minutes); maintain the system under stirring;
Add Diclofenac Potassium and wait at least 2 hours maintaining the system under stirring;
Filter the solution;
Store the solution in the selected container.

Example 42 Liquid Oral Solution with Diclofenac and High Quantity of Sorbitol as Crystallizing Sorbitol Solution, with Polyvinylpyrrolidone—14 ml Volume, (Prototype PFS DK 153-bkT038/168)

The following formulation has been prepared to obtain a ready to use liquid solution containing 50 mg of Diclofenac in 18.2 g of formula. The preparation is carried out as done for the PFS DK 87 (see Example 20) but using the Crystallizing Sorbitol Solution instead the Non-crystallizing one.
Quail/Quantitative Formulation

|   | Ingredient | mg/stick pack | % | g/bulk (4000 g) |
|---|---|---|---|---|
| 1 | Diclofenac K | 50.00 | 0.27 | 10.99 |
| 2 | Potassium Bicarbonate (KHCO3) | 22.00 | 0.12 | 4.84 |
| 3 | Crystallizing Sorbitol Solution | 18048.00 | 99.16 | 3966.59 |
| 4 | Povidone | 80.00 | 0.44 | 17.58 |
|   | Total | 18200.00 | 100.00 | 4000.00 |

Manufacturing Method
Transfer the total quantity of Non crystallizing Sorbitol Solution, in the mixer tank, under vacuum conditions;
Add all the Plasdone K29/32 and mix at regular intervals until a homogeneous solution is obtained, maintaining the apparatus under vacuum conditions;
Add Potassium Bicarbonate and Diclofenac, mix at regular intervals until a homogeneous solution is obtained, maintaining the apparatus under vacuum conditions;
Store the solution in the selected container.

Example 43 Liquid Oral Solutions with Diclofenac and High Quantity of Non Crystallizing Sorbitol Solution, with Polyvinylpyrrolidone and Differ Ent Buffering Agents—14 ml Volume The following formulation has been prepared to obtain a ready to use liquid solution containing 50 mg of Diclofenac in 18.2 g of formula. The preparations is carried out as done for the PFS DK 87 (see Example 20). The changes are the quantity of Potassium Bicarbonate or the Buffering agents (Potassium Hydroxide and Sodium Bicarbonate)
Quail/Quantitative Formulations

|   | Ingredient | PFS DK 146-F bkT038/280-F mg/stick pack | PFS DK 146 C bkT038/280-C mg/stick pack | PFS DK 146-E bkT038/280-E mg/stick pack |
|---|---|---|---|---|
| 1 | Diclofenac potassium | 50.00 | 50.00 | 50.00 |
| 2 | Potassium hydrogen carbonate | — | — | 66.00 |

-continued

| | Ingredient | PFS DK 146-F bkT038/280-F mg/stick pack | PFS DK 146 C bkT038/280-C mg/stick pack | PFS DK 146-E bkT038/280-E mg/stick pack |
|---|---|---|---|---|
| 3 | Potassium Hydroxide | 2.73 | — | — |
| 4 | Sodium Bicarbonate | — | 44.00 | — |
| 5 | Sorbitol solution (non crystallizing) | 18067.27 | 18026.00 | 18004.00 |
| 6 | Plasdone K29/32 | 80.00 | 80.00 | 80.00 |
| | Total (mg) | 18200.00 | 18200.00 | 18200.00 |
| | pH | 9.26 | 7.85 | 8.12 |

Considerations Based on the Stability Data Collected

On the basis of the data collected on the manufactured prototypes, the following considerations were made. These considerations are based on the oxidative impurities and total impurities content detected for the above-described examples; for the other parameters tested, any type of significant changes have been observed. The evaluations reported refer to samples stored both in the crimped amber vials and/or in the stick packs. The two packaging types were demonstrated to be equivalent or, in some cases, the stick packs were determined to have superior stability to crimped amber vials.

Considerations:

According to the data reported in the Example 1, Diclofenac Potassium was shown to be chemically stable for 6 months in a Non Crystallizing Sorbitol USP solution at the accelerated storage conditions. The oxidative impurities and the total impurities content are within the tentative specification limits (less than 0.2% and 1% respectively) after 6 months of storage at accelerated storage conditions. (The 6 months accelerated conditions have been tested only for samples stored in stick packs).

On the basis of the data reported in Examples 1-4, the chemical stability of Diclofenac Potassium seems to be better with the higher sorbitol concentrations.

The chemical stability of Diclofenac potassium in the different Sorbitol solutions seems independent of the manufacturing method: under N2 (Examples 1) or in open air operative conditions (Examples 5).

According to Examples 9-13, Diclofenac Potassium was chemically stable also in presence of sugars other than Non Crystallizing Sorbitol USP solution; the prototypes obtained using Xylitol (Example 9) were stable after 6 months at all the storage conditions tested. The prototypes obtained using Maltitol (Example 10), Glycerin (Example 11), Erythritol (Example 12), were stable after 6 months at all the storage conditions tested.

According to the data reported in the Example 14, Diclofenac Potassium is chemically stable in a Non Crystallizing Sorbitol USP solution, independent of the ratio between Sorbitol and Diclofenac. The total impurities content falls within the tentative specification limits (less than 1%) after 6 months of storage at the accelerated conditions.

According to the data reported in some other Examples (i.e. 15, 22, and 25), Diclofenac Potassium is chemically stable also in presence of sugars in combination with Non Crystallizing Sorbitol USP solution.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An oral liquid diclofenac formulation comprising:
   a) a therapeutically effective amount of diclofenac or a pharmaceutically acceptable salt thereof;
   b) from about 0.05% to about 9% of an alkalizing agent; and
   c) a sugar-based aqueous means for solubilizing and stabilizing the formulation, wherein the pH is from about 7 to about 10.

2. The formulation of claim 1, wherein the alkalizing agent is selected from the group consisting of ammonia solution, ammonium carbonate, diethanolamine, monoethanolamine, potassium hydroxide, sodium borate, sodium carbonate, sodium bicarbonate, sodium hydroxide, triethanolamine, and trolamine.

3. The formulation of claim 1, wherein the alkalizing agent is bicarbonate.

4. The formulation of claim 3, wherein the alkalizing agent is potassium bicarbonate.

5. The formulation of claim 1, wherein the diclofenac is diclofenac potassium.

6. The formulation of claim 1, comprising about 50 mg of diclofenac or a pharmaceutically acceptable salt thereof in from about 8 g to about 25 g of the formulation.

7. The formulation of claim 1, comprising from about 0.1% to about 1% diclofenac or a pharmaceutically acceptable salt thereof.

8. The formulation of claim 1, wherein the diclofenac is present as diclofenac potassium and the bicarbonate is present as potassium bicarbonate.

9. The formulation of claim 1, wherein the sugar-based aqueous means for solubilizing and stabilizing the formulation comprises a sugar selected from the group consisting of mono-, di-, tri-, and tetra-saccharides and sugar alcohols and combinations thereof.

10. The formulation of claim 9, wherein the sugar-based aqueous means for solubilizing and stabilizing the formulation comprises;
   a) a sugar selected from the group consisting of glucose, fructose, and galactose; or
   b) sugar alcohols selected from the group consisting of ethylene, propylene glycol, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol and polyglycitol; or
   c) a combination thereof.

11. The formulation of claim 1, further comprising a flavoring agent, wherein the flavoring agent is selected from the group consisting of acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, stevia, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, and mixtures thereof.

12. The formulation of claim 1, comprising from about 95% to about 99.85% of the sugar-based aqueous means for solubilizing and stabilizing the formulation.

13. The formulation of claim 12, wherein the sugar-based means for solubilizing and stabilizing the formulation comprises:
   a) from about 0% to about 95% water; and
   b) from about 5% to about 95% of a sugar or sugar alcohol or a combination thereof.

14. The formulation of claim 13, wherein the sugar or sugar alcohol or combination thereof comprises:
   a) from about 10% to about 90% sorbitol; and
   b) from about 10% to about 90% of xylitol, maltitol, glycerol, fructose, erythritol or a combination thereof.

15. The formulation of claim 1, wherein the sugar-based aqueous means for solubilizing and stabilizing the formulation comprises:
   a) from about 0% to about 40% water; and
   b) from about 60% to about 80% of a sugar or sugar alcohol or a combination thereof comprising:
      i) from about 10% to about 90% sorbitol; and
      ii) from about 10% to about 90% of xylitol, maltitol, glycerol, fructose, erythritol or a combination thereof.

16. The formulation of claim 1, wherein the sugar-based aqueous means for solubilizing and stabilizing the formulation comprises:
   a) from about 0% to about 60% water; and
   b) from about 40% to about 90% of sorbitol, xylitol, maltitol, glycerol, fructose, erythritol or a combination thereof.

17. The formulation of claim 1, wherein the sugar-based aqueous means for solubilizing and stabilizing the formulation comprises:
   a) from about 0% to about 75% water; and
   b) from about 25% to about 75% of xylitol.

18. The formulation of claim 1, wherein the sugar-based aqueous means for solubilizing and stabilizing the formulation comprises:
   a) from about 0% to about 75% water; and
   b) from about 25% to about 75% of maltitol.

19. The formulation of claim 1, wherein the sugar-based aqueous means for solubilizing and stabilizing the formulation comprises:
   a) from about 0% to about 75% water; and
   b) from about 25% to about 75% of glycerol.

20. The formulation of claim 1, wherein the sugar-based aqueous means for solubilizing and stabilizing the formulation comprises:
   a) from about 0% to about 75% water; and
   b) from about 25% to about 75% of fructose.

21. The formulation of claim 1, wherein the sugar-based aqueous means for solubilizing and stabilizing the formulation comprises:
   a) from about 0% to about 85% water; and
   b) from about 15% to about 45% of erythritol.

22. The formulation of claim 1, having a density of from about 1.02 to about 1.5 g/ml.

23. The formulation of claim 1, wherein the formulation comprises from about 25% to about 90% non-crystallizing sorbitol.

24. A method of treating a condition selected from pain and migraine in a patient in need thereof comprising administering to the patient a therapeutically effective amount of the formulation of claim 1.

25. A method of treating pain or migraine in a patient in need thereof comprising administering to the patient a therapeutically effective amount of the formulation of claim 8.

* * * * *